(12) United States Patent
Ota et al.

(10) Patent No.: US 10,774,087 B2
(45) Date of Patent: Sep. 15, 2020

(54) SULFONAMIDE DERIVATIVE HAVING COUMARIN SKELETON

(71) Applicant: Daiichi Sankyo Company, Limited, Chuo-ku, Tokyo (JP)

(72) Inventors: Masahiro Ota, Edogawa-ku (JP); Hidekazu Inoue, Ota-ku (JP); Junya Kawai, Ota-ku (JP); Hitoshi Ohki, Nishitokyo (JP); Tadashi Toki, Setagaya-ku (JP)

(73) Assignee: Daiichi Sankyo Company, Limited, Chuo-ku, Tokyo (JP)

( * ) Notice: Subject to any disclaimer, the term of this patent is extended or adjusted under 35 U.S.C. 154(b) by 0 days.

(21) Appl. No.: 16/463,792

(22) PCT Filed: Nov. 22, 2017

(86) PCT No.: PCT/JP2017/041944
§ 371 (c)(1),
(2) Date: May 23, 2019

(87) PCT Pub. No.: WO2018/097162
PCT Pub. Date: May 31, 2018

(65) Prior Publication Data
US 2019/0284198 A1    Sep. 19, 2019

(30) Foreign Application Priority Data
Nov. 24, 2016 (JP) .................. 2016-227429

(51) Int. Cl.
| C07D 491/052 | (2006.01) |
| A61K 31/496 | (2006.01) |
| A61P 35/00 | (2006.01) |
| A61P 43/00 | (2006.01) |

(52) U.S. Cl.
CPC ........ *C07D 491/052* (2013.01); *A61K 31/496* (2013.01); *A61P 35/00* (2018.01); *A61P 43/00* (2018.01)

(58) Field of Classification Search
CPC .... C07D 491/052; A61K 31/496; A61P 35/00
USPC ...................... 544/405; 514/252.13
See application file for complete search history.

(56) References Cited

U.S. PATENT DOCUMENTS

| 4,404,138 A | 9/1983 | Connor et al. |
| 2019/0284198 A1* | 9/2019 | Ota .................. A61P 35/00 |

FOREIGN PATENT DOCUMENTS

| JP | S59-80680 A | 5/1984 |
| WO | 2017/023894 A1 | 2/2017 |
| WO | 2017/106352 A1 | 6/2017 |
| WO | 2019/046612 A1 | 3/2019 |

OTHER PUBLICATIONS

Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Eadsforth, C.E., et al., "Acinetobacter baumannii FoID Ligand Complexes—Potent Inhibitors of Folate Metabolism and a Re-Evaluation of the Structure of LY374571," FEBS Journal 279:4350-4360, 2012.
Fu, C., et al., "The Natural Product Carolacton Inhibits Folate-Dependent C1 Metabolism by Targeting FoID/MTHFD," Nature Communications 8:1529, 2017, 9 pages.
Gustafsson, R., et al., "Crystal Structure of the Emerging Cancer Target MTHFD2 in Complex With a Substrate-Based Inhibitor," Cancer Research 77:937-948, 2017.
International Search Report and Written Opinion dated Feb. 20, 2018, issued in corresponding International Application No. PCT/JP2017/041944, filed Nov. 22, 2017, 12 pages.
Ju, H.-Q., et al., "Modulation of Redox Homeostasis by Inhibition of MTHFD2 in Colorectal Cancer. Mechanisms and Therapeutic Implications," Journal of the National Cancer Institute 111(6):1-8, 2019; published online Dec. 8, 2018.
Liu, F., et al., "Increased MTHFD2 Expression is Associated With Poor Prognosis in Breast Cancer," Tumor Biology 35:8685-8690, 2014.
Nilsson, R., et al., "Metabolic Enzyme Expression Highlights a Key Role for MTHFD2 and the Mitochondrial Folate Pathway in Cancer," Nature Communications 5:3128, 2014, 10 pages.

(Continued)

*Primary Examiner* — Venkataraman Balasubramanian
(74) *Attorney, Agent, or Firm* — Christensen O'Connor Johnson Kindness PLLC

(57) ABSTRACT

Provided is a novel compound or a salt thereof inhibiting MTHFD2 and useful for treating a disease caused by overexpression of MTHFD2, a disease involved in overexpression of MTHFD2 and/or a disease associated with overexpression of MTHFD2.
Solution
Provided is a sulfonamide derivative having a coumarin skeleton represented by the following formula (I) and having various substituents:

[Formula 1]

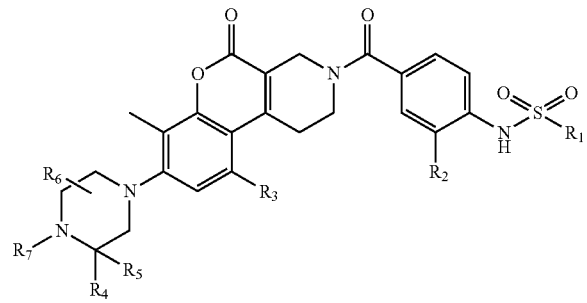

(1)

wherein $R_1$, $R_2$, $R_3$, $R_4$, $R_5$, $R_6$ and $R_7$ are the same as defined in the specification,
and a salt thereof.

5 Claims, No Drawings

(56) References Cited

OTHER PUBLICATIONS

Schmidt, A., et al., "Structures of Three Inhibitor Complexes Provide Insight into the Reaction Mechanism of the Human Methylenetetrahydrofolate Dehydrogenase/Cyclohydrolase," Biochemistry 39:6325-6335, 2000.
Tedeschi, P.M., et al., "Mitochondrial Methylenetetrahydrofolate Dehydrogenase (MTHFD2) Overexpression Is Associated with Tumor Cell Proliferation and Is a Novel Target for Drug Development," Molecular Cancer Research 13:1361-1366, 2015.
Weinberg, S.E., and N.S. Chandel, "Targeting Mitochondria Metabolism for Cancer Therapy," Nature Chemical Biology 11:9-15, 2015.
International Preliminary Report on Patentability dated May 28, 2018, issued in corresponding International Application No. PCT/JP2017/041944, filed Nov. 22, 2017, 8 pages.
Extended European Search Report dated May 20, 2020, issued in corresponding Application No. EP 17 87 4264, filed Nov. 22, 2017, 6 pages.
Patil, S., et al., "New Substituted 4H-Chromenes as Anticancer Agents," Bioorganic & Medicinal Chemistry Letters 22(13):4458-4461, Apr. 2012.
Unangst, P.C., et al., "Chromeno[3,4-c]pyridin-5-ones: Selective Human Dopamine D4 Receptor Antagonists as Potential Antipsychotic Agents," Journal of Medicinal Chemistry 40(17):2688-2693, Aug. 1997.

\* cited by examiner

SULFONAMIDE DERIVATIVE HAVING COUMARIN SKELETON

TECHNICAL FIELD

The present invention relates to a compound having a methylene-tetrahydrofolate dehydrogenase-2 (hereinafter sometimes simply referred to as MTHFD2) inhibitory activity and a medicament comprising the compound.

BACKGROUND ART

MTHFD2 is one of the isoforms of MTHFD, which is an enzyme involved in folate metabolism, and present in mitochondria. MTHFD2 is a bifunctional enzyme catalyzing a NAD+ dependent methylene-tetrahydrofolate dehydrogenase reaction and a methenyltetrahydrofolate cyclohydrolase reaction. The NAD+ dependent methylene-tetrahydrofolate dehydrogenase reaction is a reaction using 5,10-methylenetetrahydrofolate as a substrate to produce 5,10-methenyltetrahydrofolate. The methenyltetrahydrofolate cyclohydrolase reaction is a reaction using 5,10-methenyltetrahydrofolate as a substrate to produce 10-formyltetrahydrofolate.

Recently, it was reported that MTHFD2 can serve as a potential target molecule for cancer treatment (Non Patent Literature 1). More specifically, it was reported that MTHFD2 expression is remarkably enhanced in various cancers both at a mRNA level and at a protein level; and that enhancement of MTHFD2 expression is correlated with poor prognosis of breast cancer. It was also reported that if expression of MTHFD2 in cancer cells is inhibited by RNA interference, growth of the cancer cells decreases and cell death occurs significantly. MTHFD2 expression is observed in a developing embryo and is scarcely found in tissues of healthy adults even though the tissues are growing. Because of this, agents inhibiting MTHFD2 are expected to be useful as anti-cancer agents with fewer adverse drug reactions.

As compounds inhibiting MTHFD2, several folic acid analogues are known so far (Non Patent Literatures 2, 3).

CITATION LIST

Non Patent Documents

Non Patent document 1: Nilsson R. et al., Nature Communications, 2014. 5, Article number: 3128 doi:10.1038/ncomms4128.
Non Patent document 2: Schmidt A. et al., Biochemistry vol. 39 6325-6335 (2000)
Non Patent document 3: Eadsforth C. E. et al., FEBS Journal vol. 279 4350-4360 (2012)

SUMMARY OF INVENTION

Technical Problem

A compound inhibiting MTHFD2 is expected to be useful as a medicament, particularly an anticancer agent.

Solution to Problem

The present inventors conducted intensive studies. As a result, we have found a compound exerting MTHFD2 inhibitory activity, having antitumor activity and represented by the following formula (1).

The present invention relates to the following [1] to [7].

[1] A compound represented by formula (1):

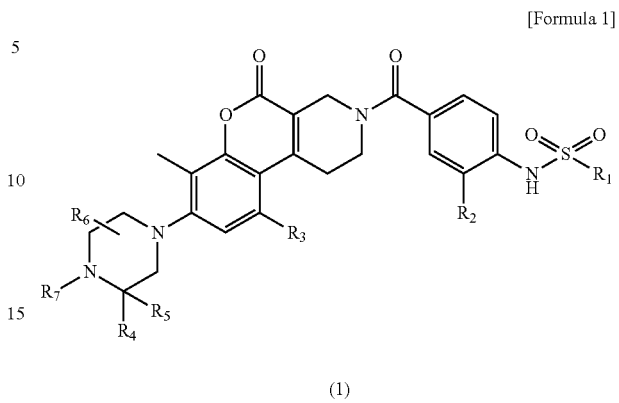

[Formula 1]

(1)

wherein,
R$_1$ represents a C$_1$ to C$_6$ alkyl group or a C$_3$ to C$_6$ cycloalkyl group,
R$_2$ represents a hydrogen atom, a halogen atom, a C$_1$ to C$_3$ alkyl group optionally substituted with 1 to 3 fluorine atoms or a C$_1$ to C$_3$ alkoxy group optionally substituted with 1 to 3 fluorine atoms,
R$_3$ represents a hydrogen atom or a C$_1$ to C$_6$ alkyl group,
R$_4$ represents a hydrogen atom or a C$_1$ to C$_6$ alkyl group,
R$_5$ represents a hydrogen atom or a C$_1$ to C$_6$ alkyl group,
R$_6$ represents a hydrogen atom or a C$_1$ to C$_6$ alkyl group,
and R$_7$ represents a hydrogen atom or a C$_1$ to C$_6$ alkyl group,
or a salt thereof.

[2] The compound or a salt thereof according to [1], wherein the compound is one selected from the group of:
N-(2-chloro-4-{[7-methyl-8-(4-methylpiperazin-1-yl)-5-oxo-1,5-dihydro-2H-chromeno[3,4-c]pyridin-3(4H)-yl]carbonyl}phenyl)methanesulfonamide,
N-(2-chloro-4-{[7-methyl-8-(4-methylpiperazin-1-yl)-5-oxo-1,5-dihydro-2H-chromeno[3,4-c]pyridin-3(4H)-yl]carbonyl}phenyl)cyclopropanesulfonamide,
N-[4-{[7-methyl-8-(4-methylpiperazin-1-yl)-5-oxo-1,5-dihydro-2H-chromeno[3,4-c]pyridin-3(4H)-yl]carbonyl}2-(trifluoromethoxy)phenyl]methanesulfonamide,
N-[2-chloro-4-({8-[(3S)-3,4-dimethylpiperazin-1-yl]-7-methyl-5-oxo-1,5-dihydro-2H-chromeno[3,4-c]pyridin-3(4H)-yl}carbonyl)phenyl]methanesulfonamide,
N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide,
N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethyl)phenyl]methanesulfonamide,
N-[2-chloro-4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)phenyl]methanesulfonamide,
N-[4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)-2-(trifluoromethoxy)phenyl]methanesulfonamide,
N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]ethanesulfonamide, N-[4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)-2-(trifluoromethoxy)phenyl]ethanesulfonamide, N-[4-({8-[(3S)-3-ethyl-4-methylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide, and N-[4-{[7-methyl-5-oxo-8-(3,3,4-trimethylpiperazin-1-yl)-1,5-dihydro-2H-chromeno[3,4-c]pyridin-3(4H)-yl]carbonyl}-2-(trifluoromethoxy)phenyl]methanesulfonamide.

[3] An MTHFD2 inhibitor comprising the compound or a salt thereof according to [1] or [2].

[4] A medicament comprising the compound or a salt thereof according to [1] or [2] as an active ingredient.

[5] An anticancer agent comprising the compound or a salt thereof according to [1] or [2] as an active ingredient.

[6] A pharmaceutical composition comprising the compound or a salt thereof according to [1] or [2] and a pharmaceutically acceptable carrier.

[7] Use of the compound or a salt thereof according to [1] or [2] for producing a medicament.

Advantageous Effects of Invention

The present invention provides a compound having MTHFD2 inhibitory activity. The compound of the present invention is useful as a medicament, particularly, an antitumor agent.

DESCRIPTION OF EMBODIMENTS

In the present invention, "MTHFD2" includes an MTHFD2 protein encoded by a full-length MTHFD2 gene or an MTHFD2 protein encoded by an MTHFD2 gene mutant (including a defective mutant, a substitution mutant and an addition mutant). In the present invention, "MTHFD2" also includes homologs derived from various animal species.

In the present invention, the terms "tumor" and "cancer" are used interchangeably. In the present invention, a tumor, a malignant tumor, a cancer, a malignant neoplasm, a carcinoma, a sarcoma and the like are sometimes collectively referred to as a "tumor" or a "cancer".

In the present invention,
the "alkyl group" refers to a linear or branched alkyl group. Examples of the "$C_1$ to $C_6$ alkyl group" include a methyl group, an ethyl group, a propyl group, an isopropyl group, a butyl group and a tert-butyl group. Examples of the "$C_1$ to $C_3$ alkyl group" include a methyl group, an ethyl group, a propyl group and an isopropyl group.

The "$C_1$ to $C_3$ alkoxy group" refers to an alkoxy group having a linear or branched $C_1$ to $C_3$ alkyl group. Examples of the "$C_1$ to $C_3$ alkoxy group" include a methoxy group, an ethoxy group, a propoxy group and an isopropoxy group.

Examples of the "halogen atom" include a fluorine atom, a chlorine atom, a bromine atom and an iodine atom.

The "$C_3$ to $C_6$ cycloalkyl group" refers to a cyclic alkyl group having 3 to 6 carbon atoms. Examples thereof include a cyclopropyl group, a cyclobutyl group, a cyclopentyl group and a cyclohexyl group.

Various substituents in formula (1) will be described below.

The present invention relates to a compound represented by the following formula (1) or a salt thereof.

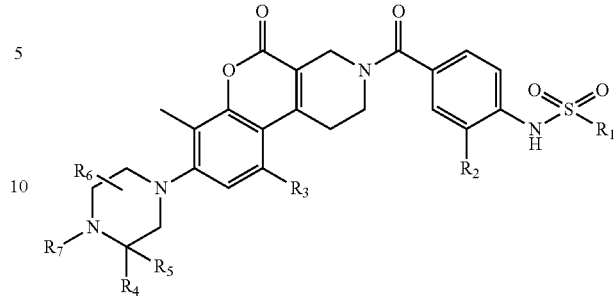

[Formula 2]

(1)

wherein, $R_1$ represents a $C_1$ to $C_6$ alkyl group or a $C_3$ to $C_6$ cycloalkyl group.

$R_1$ is preferably a methyl group, an ethyl group or a cyclopropyl group.

$R_2$ represents a hydrogen atom, a halogen atom, a $C_1$ to $C_3$ alkyl group optionally substituted with 1 to 3 fluorine atoms or a $C_1$ to $C_3$ alkoxy group optionally substituted with 1 to 3 fluorine atoms.

$R_2$ is preferably a hydrogen atom, a chlorine atom or a trifluoromethoxy group.

$R_3$ represents a hydrogen atom or a $C_1$ to $C_6$ alkyl group.
$R_3$ is preferably a hydrogen atom or a methyl group.

$R_4$ represents a hydrogen atom or a $C_1$ to $C_6$ alkyl group.
$R_4$ is preferably a hydrogen atom, a methyl group or an ethyl group.

$R_5$ represents a hydrogen atom or a $C_1$ to $C_6$ alkyl group.
$R_5$ is preferably a hydrogen atom or a methyl group.

$R_6$ represents a hydrogen atom or a $C_1$ to $C_6$ alkyl group.
$R_6$ is preferably a hydrogen atom or a methyl group.

$R_7$ represents a hydrogen atom or a $C_1$ to $C_6$ alkyl group.
$R_7$ is preferably a hydrogen atom or a methyl group.

A compound represented by formula (1) of the present invention is further preferably a compound selected from the following group:

N-(2-chloro-4-{[7-methyl-8-(4-methylpiperazin-1-yl)-5-oxo-1,5-dihydro-2H-chromeno[3,4-c]pyridin-3(4H)-yl]carbonyl}phenyl)methanesulfonamide, N-(2-chloro-4-{[7-methyl-8-(4-methylpiperazin-1-yl)-5-oxo-1,5-dihydro-2H-chromeno[3,4-c]pyridin-3(4H)-yl]carbonyl}phenyl)cyclopropanesulfonamide, N-[4-{[7-methyl-8-(4-methylpiperazin-1-yl)-5-oxo-1,5-dihydro-2H-chromeno[3,4-c]pyridin-3(4H)-yl]carbonyl}-2-(trifluoromethoxy)phenyl]methanesulfonamide, N-[2-chloro-4-({8-[(3S)-3,4-dimethylpiperazin-1-yl]-7-methyl-5-oxo-1,5-dihydro-2H-chromeno[3,4-c]pyridin-3(4H)-yl}carbonyl)phenyl]methanesulfonamide, N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide, N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethyl)phenyl]methanesulfonamide, N-[2-chloro-4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)phenyl]methanesulfonamide, N-[4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)-2-(trifluoromethoxy)phenyl]methanesulfonamide, N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]ethanesulfonamide, N-[4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)-2-(trifluoromethoxy)phenyl]ethanesulfonamide, N-[4-({8-[(3S)-3-ethyl-4-methylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide, and N-[4-{[7-methyl-5-oxo-8-(3,3,4-trimethylpiperazin-1-yl)-1,5-dihydro-2H-chromeno[3,4-c]pyridin-3(4H)-yl]carbonyl}-2-(trifluoromethoxy)phenyl]methanesulfonamide.

A compound represented by formula (1) of the present invention may have stereoisomers or optical isomers derived from asymmetric carbon atoms. The stereoisomers, optical isomers and mixtures of these are all included in the present invention.

If a compound represented by formula (1) of the present invention has a basic group such as an amino group, a pharmaceutically acceptable salt can be formed, if desired. Examples of pharmaceutically acceptable salts include hydrogen halides such as a hydrochloride and a hydroiodide; inorganic acid salts such as a nitrate, a perchlorate, a sulfate and a phosphate; lower alkane sulfonates such as a methanesulfonate, a trifluoromethanesulfonate and an ethanesulfonate; arylsulfonates such as a benzenesulfonate and a p-toluenesulfonate; organic acid salts such as a formate, an acetate, a malate, a fumarate, a succinate, a citrate, a tartrate, an oxalate and a maleate; and amino acid salts such as an ornithine salt, a glutamate and an aspartate. Hydrogen halides and organic acid salts are preferable.

If a compound represented by formula (1) of the present invention has an acidic group such as a carboxy group, generally a base addition salt can be formed. Examples of pharmaceutically acceptable salts may include alkali metal salts such as a sodium salt, a potassium salt and a lithium salt; alkaline earth metal salts such as a calcium salt and a magnesium salt; inorganic salts such as an ammonium salt; and organic amine salts such as a dibenzylamine salt, a morpholine salt, a phenylglycine alkyl ester salt, an ethylenediamine salt, a N-methylglucamine salt, a diethylamine salt, a triethylamine salt, a cyclohexylamine salt, a dicyclohexylamine salt, a N,N'-dibenzylethylenediamine salt, a diethanolamine salt, a N-benzyl-N-(2-phenylethoxy)amine salt, a piperazine salt, a tetramethylammonium salt and a tris(hydroxymethyl)aminomethane salt.

A compound represented by formula (1) of the present invention or a salt thereof may be present as the free form or a solvate, alternatively as a hydrate by absorbing moisture in the air or the like. The solvate is not particularly limited as long as it is pharmaceutically acceptable; specifically, a hydrate (e.g., monohydrate, dihydrate) and ethanol solvate are preferable. If a nitrogen atom is present in a compound represented by formula (1) of the present invention, a N-oxide may be formed. These solvates and the N-oxide are encompassed in the scope of the present invention.

A compound represented by formula (1) of the present invention may have various isomers depending on the type and combination of substituents, including geometric isomers such as a cis isomer and a trans isomer; tautomers; or optical isomers such as d-form and l-form. Unless otherwise specified, all isomers, stereoisomers and mixtures of isomers and stereoisomers, if present, in any ratio, are included as the compounds of the present invention.

A compound represented by formula (1) of the present invention may contain an atomic isotope of a single constituent atom or atomic isotopes of a plurality of constituent atoms present in a non-naturally occurring ratio. Examples of atomic isotopes include deuterium ($^2$H), tritium ($^3$H), iodine-125, ($^{125}$I) or carbon-14 ($^{14}$C). These compounds are useful as, e.g., a therapeutic or prophylactic agent, a research reagent such as an assay reagent, and a diagnostic agent such as an in-vivo imaging diagnostic agent. All isotope variants of a compound represented by formula (1) are encompassed in the scope of the present invention no matter whether radioactive or not.

The present invention also includes, a compound, which is converted into a compound represented by formula (1), which is an active ingredient of a pharmaceutical composition of the present invention, by e.g., an enzyme or a gastric acid under in-vivo physiological conditions; in other words, a compound converted into a compound represented by formula (1) through, e.g., an enzymatic oxidation, reduction or hydrolysis; and a "pharmaceutically acceptable prodrug compound", which is converted into a compound represented by formula (1) through hydrolysis with gastric acid or the like.

As the above prodrug, if an amino group is present in a compound represented by formula (1), compounds obtained by acylation, alkylation or phosphorylation of the amino group thereof (for example, a compound obtained by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group) are mentioned; if a hydroxyl group is present in a compound represented by formula (1), compounds obtained by acylation, alkylation, phosphorylation or boration of the hydroxyl group thereof (for example, a compound obtained by acetylation, palmitoylation, propanoylation, pivaloylation, succinylation, fumarylation, alanylation or dimethylaminomethylcarbonylation of the hydroxyl group) are mentioned; and if a carboxy group is present in a compound represented by formula (1), compounds obtained by esterification or amidation of the carboxy group (for example, a compound obtained by ethyl esterification, phenyl esterification, carboxymethyl esterification, dimethylaminomethyl esterification, pvaloyloxymethyl esterification, ethoxycarbonyloxyethyl esterification, amidation or methylamidation of the carboxy group) are mentioned.

A prodrug of a compound of the present invention can be produced from a compound represented by formula (1) by methods known in the art. As prodrugs of a compound of the present invention, compounds which are converted into compounds (1) under physiological conditions, as described in "Development of medicine", Vol. 7, Molecular Design, published by Hirokawa-Shoten Ltd. 1990, pages 163 to 198, are included.

A typical method for producing a compound represented by formula (1) will be described.

[Formula 3]

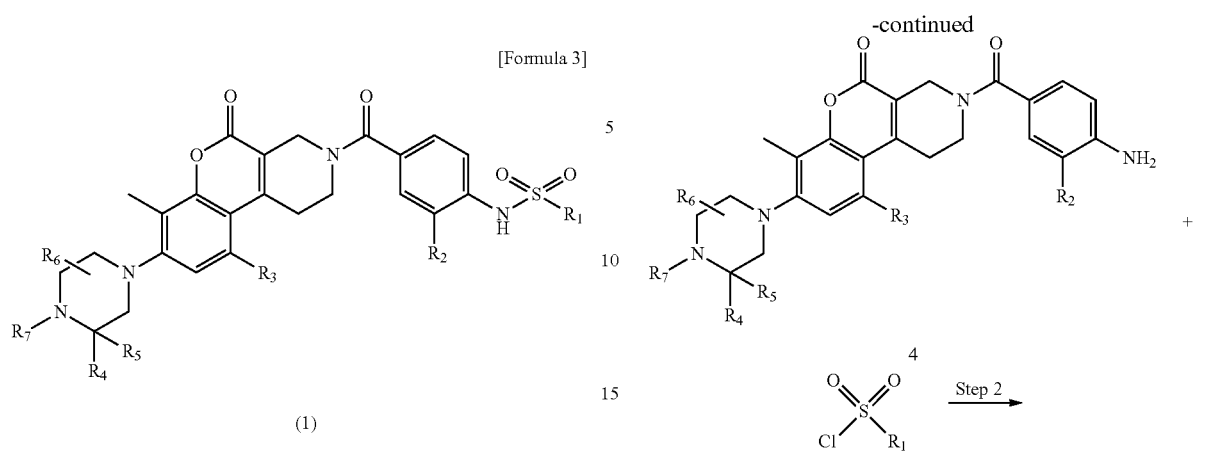

(1)

A compound of the present invention can be produced by various production methods. The production methods shown below are just examples and should not be construed as limiting the present invention. Note that, a reaction can be carried out, if necessary, by protecting a substituent(s) by an appropriate protecting group. The type of protecting group is not particularly limited.

A compound represented by formula (1) (sometimes referred to as a compound (1)) can be produced from compound 2 separately produced, in accordance with, for example, the reaction scheme shown below. For example, a method of producing a compound (1) via compound 4, which is produced from compound 2 and compound 3; and a method of producing a compound (1) in a single step of reacting compound 2 and compound 6 produced separately, are known.

In the formula, $R_1$ to $R_7$ are the same as defined above.

[Formula 4]

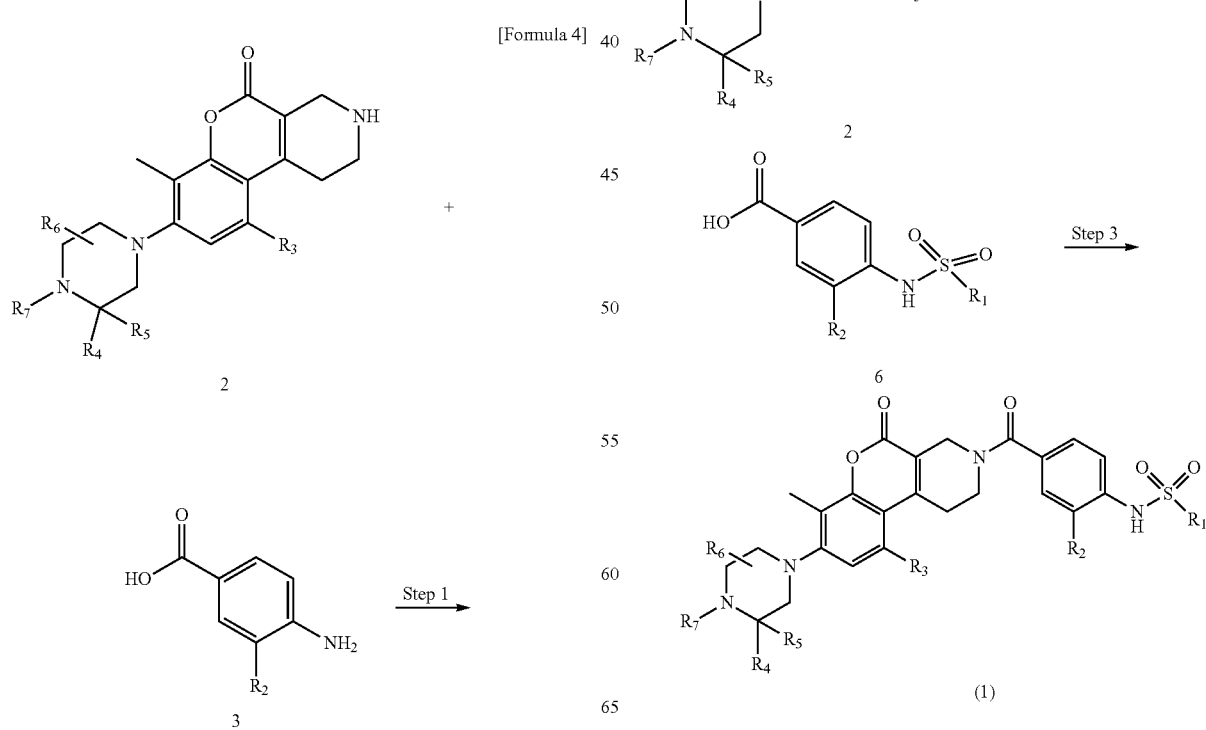

Step 1

Compound 2 is converted into compound 4 through an amidation reaction between compound 2 and compound 3 having a partial structure containing $R_2$ in accordance with an organic chemical technique known in the art. The amidation reaction is carried out by reacting a carboxylic acid compound 3 with compound 2 in an appropriate solvent having no adverse effect on the reaction (e.g., benzene, toluene, diethyl ether, dichloromethane, tetrahydrofuran or N,N-dimethylformamide) or in a mixed solvent of these, in the range from −30° C. to the boiling point of the solvent used in the reaction, preferably from 0° C. to 50° C., in the presence of an appropriate condensing agent such as N,N-dicyclohexylcarbodiimide, 1-ethyl-3-(3-dimethylaminopropyl) carbodiimide, diethyl cyanophosphate, N-[1-(cyano-2-ethoxy-2-oxoethylidene aminooxy) dimethylamino (morpholino)]uronium hexafluorophosphate (COMU) and N,N,N',N'-tetramethyl-O-(7-azabenzotriazol-1-yl)uronium hexafluorophosphate (HATU).

The condensing agent may be used in excessive molar equivalents to the compound, preferably 1 to 5 molar equivalents. The reaction may be carried out by using a base (for example, triethylamine, diisopropylethylamine, N-methylmorpholine or 4-dimethylaminopyridine), if needed. The amount of the base that can be used may be a catalytic amount or an excess amount.

The reaction time is preferably from 10 minutes to 72 hours; however, the reaction time is not particularly limited. The reaction is carried out by using additives known as reaction accelerators (e.g., 1-hydroxybenzotriazole, 1-hydroxy-7-azabenzotriazole), if needed. The amount of the reaction accelerator that can be used may be within the range of a catalytic amount to an excess amount.

In place of compound 2, a salt of compound 2 (e.g., hydrochloride, sulfate) also can be used.

Step 2

Compound 4 is converted into compound (1) by a sulfonamidation reaction of compound 4, which is carried out in an appropriate solvent having no adverse effect on the reaction (for example, dichloromethane, toluene, tetrahydrofuran, acetone) or in mixed solvent of these, in the presence of a base (for example, pyridine, triethylamine, diisopropylethylamine, 4-methylmorpholine, 4-dimethylaminopyridine) by using, e.g., sulfonyl chloride (compound 5) having $R_1$ or a corresponding sulfonic acid anhydride. Note that, a base such as pyridine can simultaneously be used also as a solvent. Sulfonyl chloride may be used usually in one to excess molar equivalent to compound 4. The reaction temperature usually falls within the range from 0° C. to the boiling point of the solvent, and preferably falls within the range of 0° C. to 100° C. The reaction time is preferably 10 minutes to 72 hours but is not particularly limited.

Depending on the reaction conditions, a disulfonyl form is obtained in some cases by reacting two sulfonyl-chloride molecules. In this case, the disulfonyl form can be converted into compound (1) by a treatment with an excess amount of an alkali (e.g., lithium hydroxide, sodium hydroxide, potassium hydroxide) performed in an appropriate solvent (for example, tetrahydrofuran, dioxane, water) having no adverse effect on the reaction, or a mixed solvent of these. The amount of the alkali is, e.g., 1 to 10 equivalents relative to compound 5. The reaction temperature falls within the range of 0° C. to 100° C. and preferably falls within the range of 0° C. to 50° C.

Step 3

If compound (1) is produced by directly reacting compound 2 and compound 6 produced separately, the reaction can be carried out by the same amidation reaction as in Step 1.

Compound 2 can be produced, for example, in accordance with the following reaction scheme. In the following reaction, a tert-butoxycarbonyl group (Boc group) is used as a protecting group; however, an appropriate protecting group other than this can be used for production depending on the type of functional groups in compound 12. In this case, step 8 (deprotection step) may be appropriately changed depending on the type of protecting group, to produce compound 2.

[in the scheme, $R_3$ to $R_7$ are the same as defined above; and $R_8$ represents a hydrogen atom or a $C_1$ to $C_6$ alkyl group]

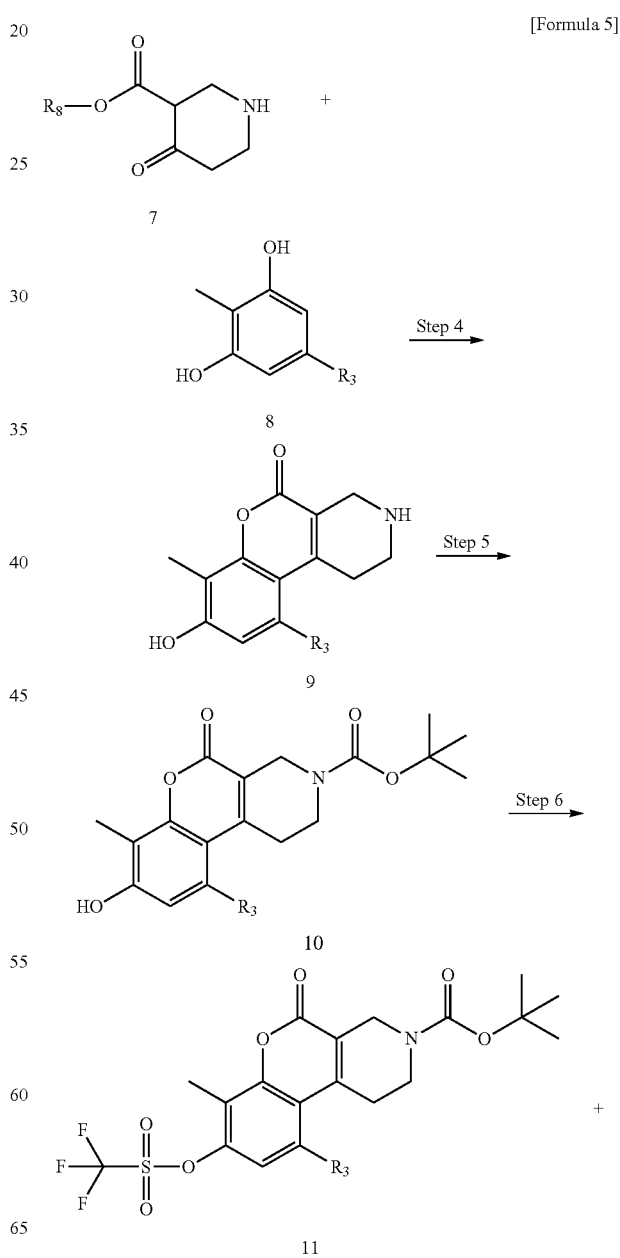

[Formula 5]

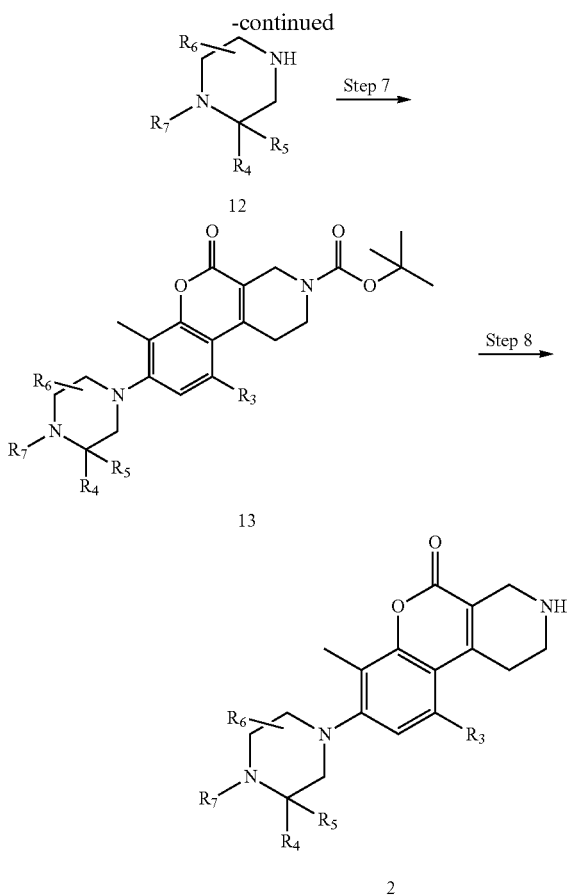

compound 11 can be produced by allowing a triflating reagent such as trifluoromethanesulfonic anhydride or N,N-bis(trifluoromethylsulfonyl) aniline to react with compound 10 in an appropriate solvent having no adverse effect on the reaction (for example, dichloromethane, chloroform, toluene, acetonitrile) or a mixed solvent of these, in the presence of a base (for example, pyridine, triethylamine, diisopropylethylamine, 2,6-lutidine). The reaction temperature is usually about −10° C. to 30° C. Note that, a base such as pyridine may simultaneously be used also as a solvent.

Step 7

Step 7 is a step of producing compound 13 by the Buchwald reaction between compound 11 and amine 12. For example, the step can be carried out by subjecting compound 11 and a compound 12 having a partial structure containing $R_4$ to $R_7$, to a coupling reaction in an appropriate solvent having no adverse effect on the reaction (for example, toluene, xylene, 1,4-dioxane, tetrahydrofuran) or a mixed solvent of these, in the presence of a palladium catalyst, a phosphine ligand and a base.

Compound 12 may be used in excess in terms of molar equivalent to compound 11; preferably 1 to 5 molar equivalents may be used. Examples of the palladium catalyst include palladium acetate (II), tris(benzylideneacetone)dipalladium (0), bis(triphenylphosphine)palladium chloride (II), 1,1'-bis(diphenylphosphino)ferrocenedichloropalladium (II) dichloromethane complex, and chloro-(2-dicyclohexylphosphino-2',6'-diisopropoxy-1,1'-biphenyl)[2-(2-aminoethyl)phenyl]palladium (II)-methyl-t-butyl ether adduct. Examples of the phosphine ligand include BINAP, dppf, Dav-Phos, JohnPhos, c-Hexyl JohnPhos, S-Phos, X-Phos, Xantphos and RuPhos. Examples of the base include sodium t-butoxide, potassium carbonate, sodium carbonate, cesium carbonate and potassium phosphate. The palladium catalyst is used in a ratio of 0.01 to 1 equivalent to compound 11 and preferably 0.05 to 0.5 equivalents. The phosphine ligand is used in a ratio of 0.01 to 1 equivalent to compound 11 and preferably 0.05 to 0.5 equivalents. The base is used in a ratio of 1 to 10 molar equivalents to compound 11 and preferably 2 to 5 molar equivalents. The reaction temperature usually falls within the range of room temperature to the boiling point of the solvent and preferably room temperature to 150° C. The above reaction can be carried out in a sealed tube by application of microwaves.

The reaction time, which varies depending on the amount of catalyst and the reaction temperature, is usually 1 to 100 hours and preferably 1 to 50 hours.

Step 8

The Boc group of compound 13 can be removed in accordance with a method known in the art, by treatment with an acid (examples thereof include, but are not particularly limited to, hydrogen chloride, sulfuric acid, trifluoro acetic acid) performed in an appropriate solvent having no adverse effect on the reaction (e.g., chloroform, dichloromethane, diethyl ether, dioxane, toluene, water) or a mixed solvent of these. The amount of acid that can be used relative to compound 13 can be e.g., 1 to 100 moles and preferably 1 to 10 moles. The reaction temperature usually falls within the range of 0° C. to 100° C. and preferably falls within the range of 0° C. to 50° C. The reaction time, which varies depending on the amount of acid and the reaction temperature, is usually 10 minutes to 100 hours.

Compound 6 can be synthesized from compound 14 via compound 15 by reference to descriptions in previous reports such as Bioorg. Med. Chem. 2009, 17, 1307, Chem. Pharm. Bull. 1999, 47, 809.

Step 4

Conversion from compound 7 to compound 9 can be carried out by a condensation reaction of e.g., β-ketocarboxylic acid (or ester) 7 and resorcinol 8 containing a partial structure including $R_3$ in sulfuric acid under the reaction condition known as the Pechmann reaction. The concentration of sulfuric acid used is usually 64% to 98%, but is not particularly limited. The reaction temperature usually falls within the range of 0° C. to 100° C. and preferably falls within the range of 0° C. to 50° C. The reaction time, which varies depending on the concentration of sulfuric acid and the reaction temperature, is usually 10 minutes to 100 hours.

Step 5

Conversion from compound 9 to compound 10 can be carried out by a tert-butoxycarbonylation (Boc) reaction known in the art; for example, by allowing di-tert-butyl dicarbonate to react with compound 9 in an appropriate solvent having no adverse effect on the reaction (for example, tetrahydrofuran, dioxane, ethyl acetate, toluene, dichloromethane, N,N-dimethylformamide) or a mixed solvent of these, in the presence of a base (for example, an organic base such as pyridine and triethylamine or an aqueous solution of an inorganic base such as sodium hydroxide, sodium carbonate and sodium hydrogen carbonate). The reaction temperature usually falls within the range of 0° C. to 100° C. and preferably falls within the range of 0° C. to 50° C. The reaction time is usually 10 minutes to 100 hours.

Step 6

Conversion from compound 10 to compound 11 can be carried out by triflation known in the art. For example,

[in the scheme, $R_1$ and $R_2$ are the same as defined above; and $R_9$ represents a protecting group for carboxylic acid such as a $C_1$-$C_6$ alkyl group]

[Formula 6]

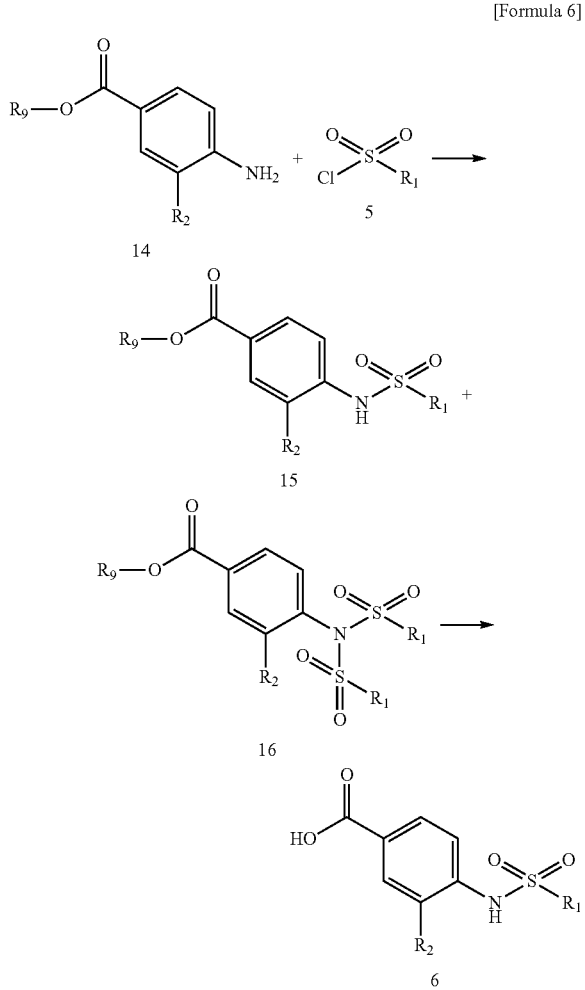

Conversion from compound 14 to compound 6

Compound 6 can be converted from compound 14 via compound 15 by a two-step reaction, i.e., sulfonamidation and alkaline hydrolysis of compound 14, which is commercially available or appropriately synthesized. In the sulfonamidation reaction, compound 16 may be obtained by reacting 2 molecules of sulfonyl chloride. In this case, compound 16 or a mixture of compound 15 and compound 16 without their isolation may be subjected to alkaline hydrolysis. In this manner, a desulfonylation reaction and an ester hydrolysis reaction can simultaneously be carried out to produce compound 6.

The sulfonamidation reaction can be carried out in the same manner as in the conversion from compound 4 to compound (1).

The alkaline hydrolysis reaction can be carried out by treatment with an excess amount of alkali (e.g., lithium hydroxide, sodium hydroxide, potassium hydroxide) performed in an appropriate solvent having no adverse effect on the reaction (for example, tetrahydrofuran, dioxane, water) or a mixed solvent of these. As the amount of alkali, about 2 to 10 equivalents may be used relative to compound 14 and compound 5. The reaction temperature falls within the range of 0° C. to 100° C. and preferably falls within the range of 0° C. to 50° C.

Raw materials 3, 5, 7, 8 and 12 may be commercially available products or can be synthesized in accordance with methods known in the art.

In place of compound 12, a salt of compound 12 can be used.

In an embodiment of the present invention, since a compound represented by formula (1) or a salt thereof inhibits MTHFD2, the compound or a salt thereof is used as an MTHFD2 inhibitor.

The inhibitory activity of MTHFD2 can be measured, for example, by the method described in the Experimental Example of the present application; however, the method is not limited to this.

A compound represented by formula (1) or a salt thereof has cancer cell growth inhibitory activity, and thus, can be used as a medicament, preferably an antitumor agent or an anticancer agent comprising the compound.

Cell growth inhibitory activity can be determined by a growth inhibition test method ordinarily used by a person skilled in the art. Cell growth inhibitory activity is determined, for example, by comparing a degree of cell growth (for example, tumor cells) between in the presence and absence of a test compound, as described in Experimental Example 2 (later described). The degree of cell growth can be determined by a test system for counting living cells. As the method for counting living cells, for example, [$^3$H]-thymidine uptake test, BrdU method or MTT assay is mentioned.

In-vivo antitumor activity can be determined by use of an antitumor test method ordinarily used by a person skilled in the art. For example, any of various types of tumor cell is transplanted in, e.g., mice or rats. After engraftment of transplanted cells is confirmed, a compound of the present invention is orally or intravenously administered. Several days to a few weeks after the administration, tumor growth in a non-drug administration group is compared to that of a compound administration group. In this manner, the in-vivo antitumor activity of the present invention can be confirmed.

A compound of the present invention can be used for treatment of a tumor or a cancer such as lung cancer, gastrointestinal cancer, ovarian cancer, uterine cancer, breast cancer, prostate cancer, liver cancer, head and neck cancer, blood cancer, kidney cancer, skin cancer (e.g., malignant melanoma), retinoblastoma, testicular tumor, sarcoma; and more preferably, lung cancer, breast cancer, prostate cancer, colon cancer, acute myelogenous leukemia, malignant lymphoma, malignant melanoma, retinoblastoma, neuroblastoma or sarcoma; however the cancers are not limited to these.

The medicament of the present invention contains a compound of the present invention and a pharmaceutically acceptable carrier and can be administered as an injection such as an intravenous injection, an intramuscular injection and a subcutaneous injection, or administered by a method such as oral administration or transdermal administration. The pharmaceutically acceptable carrier refers to a pharmaceutically acceptable material (for example, excipient, diluent, additive, solvent) involved in transporting a composition comprising a compound of the present invention or a salt thereof from an organ to another organ.

Preparations (for example, oral preparation or injection) can be appropriately selected in accordance with the administration method. The preparation can be produced by a preparation method ordinarily employed. As an oral preparation, for example, a tablet, a powder, a granule, a capsule, a pill, a lozenge, a solution, a syrup, an elixir, an emulsion, or an oil or aqueous suspension, can be mentioned. In the case of oral administration, a compound can be used in the free form or a salt form. An aqueous preparation can be prepared by forming an acid adduct with a pharmaceutically acceptable acid or an alkali metal salt such as a sodium salt. In the case of an injection, e.g., a stabilizer, a preservative or a solubilizing agent can be used in the preparation. A solution optionally containing these pharmaceutical aids is stored in a container and, e.g., lyophilized to prepare a solid preparation, which is thawed and re-prepared when used. A single dose or multiple doses may be stored in a single container.

As solid preparations, for example, a tablet, a powder, a granule, a capsule, a pill or a lozenge is mentioned. These solid preparations may contain pharmaceutically acceptable additives together with a compound of the present invention or a salt thereof. As additives, for example, a filler, a thickening agent, a binder, a disintegrant, a dissolution accelerator, a wetting agent and a lubricant are mentioned. These can be optionally used and mixed to produce a preparation.

As liquid preparations, for example, a solution, a syrup, an elixir, an emulsion or a suspending agent is mentioned. These liquid preparations may contain a pharmaceutically acceptable additives together with a compound of the present invention or a salt thereof. As additives, for example, a suspending agent or an emulsifier is mentioned. These may be optionally used and mixed to produce a preparation.

A compound of the present invention or a salt thereof can be used in cancer treatment for a mammal, particularly, a human. Dosage and administration interval are appropriately selected at a doctor's discretion depending on the site of disease, or the height, body weight, sex and medical history of the patient. When a compound of the present invention is administered to a human, the range of daily dose is about 0.01 mg/kg body weight to about 500 mg/kg body weight, and preferably, about 0.1 mg/kg body weight to about 100 mg/kg body weight. When a compound of the present invention is administered to a human, the dose is administered preferably once daily or by dividing into two to four portions daily and administered at appropriate intervals. The daily dose may exceed the aforementioned amount at a doctor's discretion, if necessary.

A compound of the present invention or a salt thereof may be used in combination with another antitumor agent. Examples thereof include an alkylating agent, a metabolic antagonist, an antitumor antibiotic substance, an antitumor plant component, a biological response modifier (BRM), a hormone, a vitamin, an antitumor antibody, a molecular targeting drug and other antitumor agents.

More specifically, examples of alkylating agents include an alkylating agent such as nitrogen mustard, nitrogen mustard N-oxide or chlorambucil, an aziridine alkylating agent such as carboquone or thiotepa, an epoxide alkylating agent such as dibromomannitol or dibromodulcitol, a nitrosourea alkylating agent such as carmustine, lomustine, semustine, nimustine hydrochloride, streptozocin, chlorozotocin or ranimustine, busulfan, improsulfan tosylate or dacarbazine.

As metabolic antagonists, for example, a purine metabolic antagonist, such as 6-mercaptopurine, 6-thioguanine or thioinosine; a pyrimidine metabolic antagonist such as fluorouracil, tegafur, tegafur uracil, carmofur, doxifluridine, broxuridine, cytarabine or enocitabine; or a folate metabolic antagonist such as a methotrexate or trimetrexate is mentioned.

As antitumor antibiotic substances, for example, an anthracycline antibiotic substance/antitumor agent such as mitomycin C, bleomycin, peplomycin, daunorubicin, aclarubicin, doxorubicin, pirarubicin, THP-adriamycin, 4'-epidoxolubicin or epirubicin; or chromomycin A3 or actinomycin D is mentioned.

As antitumor plant components, for example, a vinca alkaloid such as vindesine, vincristine or vinblastine; a taxane such as paclitaxel or docetaxel; or an epipodophyllotoxin such as etoposide or teniposide is mentioned.

As BRM, for example, a tumor necrosis factor or indomethacin is mentioned.

As hormones, for example, hydrocortisone, dexamethasone, methyl prednisolone, prednisolone, prasterone, betamethasone, triamcinolone, oxymetholone, nandrolone, methenolone, fosfestrol, ethynyl estradiol, chlormadinone or medroxyprogesterone is mentioned.

As vitamins, for example, vitamin C or vitamin A is mentioned.

As antitumor antibodies and molecular targeting drugs, trastuzumab, rituximab, cetuximab, nimotuzumab, denosumab, bevacizumab, infliximab, imatinib mesylate, gefitinib, erlotinib, sunitinib, lapatinib, sorafenib or osimertinib is mentioned.

As antitumor agents other than those mentioned above, for example, cisplatin, carboplatin, oxaliplatin, tamoxifen, camptothecin, ifosfamide, cyclophosphamide, melphalan, L-asparaginase, aceglatone, schizophyllan, picibanil, procarbazine, pipobroman, neocarzinostatin, hydroxyurea, ubenimex or krestin or an immune checkpoint inhibitor such as nivolumab or pembrolizumab is mentioned.

The present invention includes a method for preventing and/or treating cancer characterized by administering a compound of the present invention or a salt thereof.

The present invention further includes use of a compound of the present invention or a salt thereof for producing a medicament as mentioned above.

The present invention also includes a compound of the present invention or a salt thereof for use in treatment or prevention of cancer.

The present invention will be more specifically described by way of the Examples shown below; however, the present invention is not limited to these examples. These should not be construed as limiting the invention. In the specification, unless otherwise specified, reagents, solvents and starting materials can easily be obtained from commercially available supply sources.

EXAMPLES

In NMR data, unless otherwise specified, measurement was carried out at about 20° C.

Example 1

[Step 1] 8-Hydroxy-7-methyl-1,2,3,4-tetrahydro-5H-chromeno[3,4-c]pyridin-5-one 1/2 sulfate

[Formula 7]

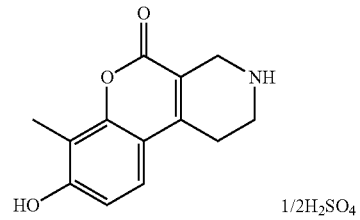

1/2H$_2$SO$_4$

To ethyl 4-oxopiperidine-3-carboxylate hydrochloride (40.5 g) and 2-methylbenzene-1,3-diol (24.2 g), 64% sulfuric acid (200 ml) was added. The reaction solution was stirred at room temperature for 6 hours and allowed to stand overnight. Ice water (300 ml) was added and the resultant reaction solution was stirred for 2 hours.

Insoluble matter was collected by filtration, washed with a small volume of water and hexane, then dried at 50° C. under reduced pressure to obtain the title compound (45.1 g) as a solid.

$^1$H-NMR (DMSO-D$_6$, 50° C.) δ: 7.42 (1H, d, J=8.5 Hz), 6.89 (1H, d, J=8.5 Hz), 3.78 (2H, s), 3.23-3.18 (3H, m), 2.88 (2H, t, J=5.8 Hz), 2.18 (3H, s).

MS (ESI/APCI) m/z: 232 [M+H]+

[Step 2] tert-Butyl 8-hydroxy-7-methyl-5-oxo-1,5-dihydro-2H-chromeno[3,4-c]pyridine-3(4H)-carboxylate

[Formula 8]

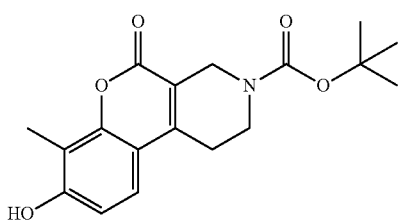

To a suspension of 8-hydroxy-7-methyl-1,2,3,4-tetrahydro-5H-chromeno[3,4-c]pyridin-5-one 1/2 sulfate (5.02 g) in tetrahydrofuran (100 ml), 1 N sodium hydroxide solution (15.2 ml) was added. The reaction solution was stirred at room temperature for 30 minutes. A saturated aqueous solution of sodium hydrogen carbonate (30 ml) and di-tert-butyl dicarbonate (3.5 g) were added and the resultant reaction solution was stirred for 3 hours and then allowed to stand overnight. The reaction solution was diluted with ethyl acetate. The organic layer was washed with water, dried over anhydrous sodium sulfate, filtered and then concentrated. To the residue, ethyl acetate was added and insoluble matter was collected by filtration, dried at 60° C. under reduced pressure to obtain the title compound (4.32 g) as a solid.

$^1$H-NMR (DMSO-D$_6$) δ: 10.37 (1H, s), 7.41 (1H, d, J=8.5 Hz), 6.87 (1H, d, J=8.5 Hz), 4.19 (2H, s), 3.61 (2H, t, J=5.5 Hz), 2.83 (2H, t, J=5.8 Hz), 2.16 (3H, s), 1.44 (9H, s).

MS (ESI/APCI) m/z: 276 [M-tBu+H]+

[Step 3] tert-Butyl 7-methyl-5-oxo-8-{[(trifluoromethyl)sulfonyl]oxy}-1,5-dihydro-2H-chromeno[3,4-c]pyridine-3(4H)-carboxylate

[Formula 9]

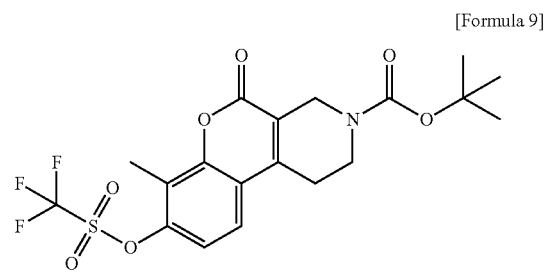

To a suspension of tert-butyl 8-hydroxy-7-methyl-5-oxo-1,5-dihydro-2H-chromeno[3,4-c]pyridine-3(4H)-carboxylate (6.43 g) and pyridine (2.82 ml) in dichloromethane (100 ml), trifluoromethanesulfonic anhydride (4.24 ml) was added under ice cooling. The reaction solution was stirred at 0° C. for 30 minutes and then water was added. The reaction solution was extracted with chloroform. The organic layer was washed with 0.25 N hydrochloric acid and saturated saline, dried over anhydrous sodium sulfate and then filtered. After the solvent was evaporated under reduced pressure, the residue was purified by silica gel chromatography (0-2% methanol/methylene chloride) to obtain the title compound (8.09 g) as a solid.

$^1$H-NMR (CDCl$_3$) δ: 7.49 (1H, d, J=8.5 Hz), 7.29-7.24 (1H, m), 4.43 (2H, s), 3.75 (2H, t, J=5.8 Hz), 2.88 (2H, s), 2.49 (3H, s), 1.50 (9H, s).

[Step 4] tert-Butyl 7-methyl-8-(4-methylpiperazin-1-yl)-5-oxo-1,5-dihydro-2H-chromeno[3,4-c]pyridine-3(4H)-carboxylate

[Formula 10]

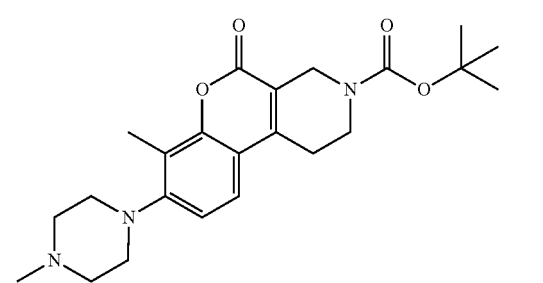

To a suspension of tert-butyl 7-methyl-5-oxo-8-{[(trifluoromethyl)sulfonyl]oxy}-1,5-dihydro-2H-chromeno[3,4-c]pyridine-3(4H)-carboxylate (5.60 g) in toluene (100 ml), cesium carbonate (5.91 g), chloro-(2-dicyclohexylphosphino-2',6'-diisopropoxy-1,1'-biphenyl)[2-(2-aminoethyl)phenyl]palladium (II)-methyl-t-butyl ether adduct (250 mg), 2-dicyclohexylphosphino-2',6'-diisopropoxybiphenyl (141 mg) and 1-methylpiperazine (3.33 ml) were added. The reaction solution was stirred in a nitrogen atmosphere at 110° C. for 8 hours while heating. The reaction solution was diluted with chloroform and a small volume of methanol and filtered with Celite. The reaction solution, to which water and saturated saline were added, was extracted with chloroform and a small volume of methanol. The organic layer was dried over anhydrous sodium sulfate and then filtered. The filtrate was concentrated under reduced pressure. The residue was purified by silica gel column chromatography (1-10% methanol/chloroform) to obtain the title compound (4.59 g) as a solid.

$^1$H-NMR (CDCl$_3$) δ: 7.36 (1H, d, J=8.5 Hz), 6.99 (1H, d, J=8.5 Hz), 4.40 (2H, s), 3.72 (2H, t, J=5.8 Hz), 3.02 (4H, t, J=4.6 Hz), 2.88-2.82 (2H, m), 2.66-2.57 (2H, m), 2.38 (6H, s), 1.66-1.59 (2H, m), 1.49 (9H, s).

MS (ESI/APCI) m/z: 414 [M+H]+

[Step 5] 7-Methyl-8-(4-methylpiperazin-1-yl)-1,2,3,4-tetrahydro-5H-chromeno[3,4-c]pyridin-5-one dihydrochloride

[Formula 11]

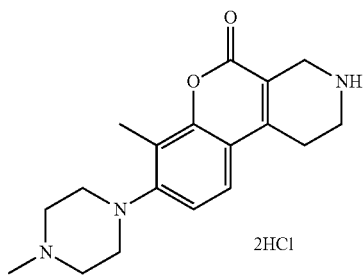

2HCl

To a solution of tert-butyl 7-methyl-8-(4-methylpiperazin-1-yl)-5-oxo-1,5-dihydro-2H-chromeno[3,4-c]pyridine-3(4H)-carboxylate (4.59 g) in methanol (50 ml), 4 N hydrochloric acid/1,4-dioxane (50 ml) was added. The reaction solution was stirred at room temperature for 2 hours. The reaction solution was concentrated under reduced pressure. To the residue, a small volume of methanol, ethyl acetate and hexane were added and insoluble matter was collected by filtration and dried under reduced pressure to obtain the title compound (3.92 g) as a solid.

$^1$H-NMR (DMSO-D$_6$, 80° C.) δ: 9.79 (1H, s), 7.60 (1H, d, J=8.5 Hz), 7.14 (1H, d, J=8.5 Hz), 3.97 (2H, s), 3.41 (2H, t, J=6.1 Hz), 3.30-3.25 (4H, m), 3.17-3.10 (8H, m), 2.82 (3H, s), 2.33 (3H, s).

MS (ESI/APCI) m/z: 314 [M+H]+

[Step 6] 3-(4-Amino-3-chlorobenzoyl)-7-methyl-8-(4-methylpiperazin-1-yl)-1,2,3,4-tetrahydro-5H-chromeno[3,4-c]pyridin-5-one

[Formula 12]

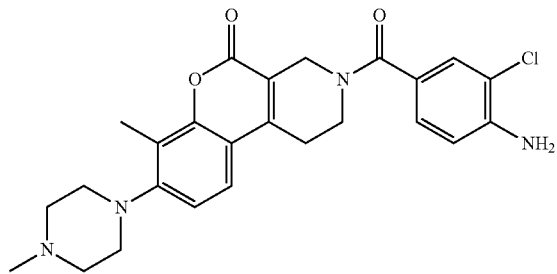

To a suspension of 7-methyl-8-(4-methylpiperazin-1-yl)-1,2,3,4-tetrahydro-5H-chromeno[3,4-c]pyridin-5-one dihydrochloride (600 mg), 4-amino-3-chlorobenzoic acid (294 mg), 3H-1,2,3-triazolo[4,5-b] pyridin-3-ol (233 mg) and 1-ethyl-3-(3-dimethylaminopropyl)carbodiimide hydrochloride (372 mg) in N,N-dimethylformamide (10 ml), N,N-diisopropylethylamine (1.35 ml) was added. The reaction solution was stirred at room temperature for 4 hours and then allowed to stand at room temperature for 3 days. To the reaction solution, water was added and insoluble matter was collected by filtration, washed with water and hexane and dried at 60° C. under reduced pressure to obtain the title compound (650 mg) as a solid.

MS (ESI/APCI) m/z: 467 (M+H)+

$^1$H-NMR (DMSO-D$_6$, 50° C.) δ: 7.53 (1H, d, J=8.5 Hz), 7.35 (1H, d, J=2.1 Hz), 7.20 (1H, dd, J=8.2, 2.1 Hz), 7.07 (1H, d, J=9.2 Hz), 6.82 (1H, d, J=8.5 Hz), 5.73 (2H, s), 4.40-4.38 (2H, m), 3.79-3.75 (2H, m), 2.97-2.93 (6H, m), 2.54-2.50 (4H, m), 2.28 (3H, s), 2.26 (3H, s).

[Step 7] N-(2-chloro-4-{[7-methyl-8-(4-methylpiperazin-1-yl)-5-oxo-1,5-dihydro-2H-chromeno[3,4-c]pyridin-3(4H)-yl]carbonyl}phenyl)methanesulfonamide

[Formula 13]

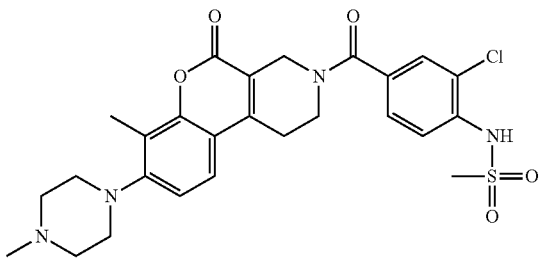

To a suspension of 3-(4-amino-3-chlorobenzoyl)-7-methyl-8-(4-methylpiperazin-1-yl)-1,2,3,4-tetrahydro-5H-chromeno[3,4-c]pyridin-5-one (650 mg) in dichloromethane (30 ml), triethylamine (0.98 ml) and methanesulfonyl chloride (0.38 ml) were added dropwise under ice cooling. The reaction solution was stirred for 2 hours. The solvent was evaporated under reduced pressure. To the residue, tetrahydrofuran (15 ml) was added and the reaction solution was stirred under ice cooling. A 1 N aqueous solution of sodium hydroxide (14 ml) was added and the resultant reaction solution was stirred overnight, neutralized with 1 N hydrochloric acid to pH=7 to 8, concentrated under reduced pressure and extracted three times with methylene chloride. The organic layer was dried with anhydrous sodium sulfate and then filtered. The solution was concentrated under reduced pressure and the residue was purified by silica gel column chromatography (4-12% methanol/methylene chloride). The purified product was suspended in ethyl acetate and heated to reflux for one hour. After the product was allowed to cool, insoluble matter was collected by filtration, dried at 60° C. under reduced pressure to obtain the title compound (566 mg) as a solid.

$^1$H-NMR (DMSO-D$_6$, 80° C.) δ: 9.33 (1H, s), 7.60 (1H, d, J=1.8 Hz), 7.57-7.49 (2H, m), 7.43 (1H, dd, J=8.5, 1.8 Hz), 7.07 (1H, d, J=8.5 Hz), 4.40 (2H, s), 3.80-3.73 (2H, m), 3.10 (3H, s), 2.99-2.94 (6H, m), 2.58-2.53 (4H, m), 2.29 (6H, s).

MS (ESI/APCI) m/z: 545 [M+H]+

Example 2

N-(2-Chloro-4-{[7-methyl-8-(4-methylpiperazin-1-yl)-5-oxo-1,5-dihydro-2H-chromeno[3,4-c]pyridin-3(4H)-yl]carbonyl}phenyl)cyclopropanesulfonamide

[Formula 14]

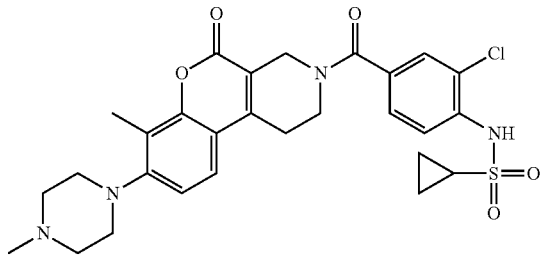

To a suspension of 3-(4-amino-3-chlorobenzoyl)-7-methyl-8-(4-methylpiperazin-1-yl)-1,2,3,4-tetrahydro-5H-chromeno[3,4-c]pyridin-5-one (50 mg) in pyridine (1.8 ml), 4-dimethylaminopyridine (6.5 mg) and cyclopropanesulfonyl chloride (0.022 ml) were added. The reaction solution was heated by use of microwaves at 140° C. for one hour. To the reaction solution, cyclopropanesulfonyl chloride (0.065 ml) was further added. The reaction solution was heated by use of microwaves at 140° C. for one hour. The temperature of the reaction solution was returned to room temperature and the reaction solution was concentrated. The residue was purified sequentially by silica gel chromatography (3-12% methanol/methylene chloride) and amino-silica gel chromatography (10-50% methanol/methylene chloride) to obtain the title compound (11 mg).

MS (ESI/APCI) m/z: 571 [M+H]+

$^1$H-NMR (DMSO-D$_6$, 80° C.) δ: 0.90-0.96 (4H, m), 2.26 (3H, s), 2.28 (3H, s), 2.49-2.54 (4H, m), 2.60-2.69 (1H, m), 2.93-2.97 (6H, m), 3.73-3.81 (2H, m), 4.39 (2H, s), 7.07 (1H, d, J=9.1 Hz), 7.36 (1H, d, J=8.5 Hz), 7.49-7.56 (3H, m).

Example 3

[Step 1] 3-[4-Amino-3-(trifluoromethoxy)benzoyl]-7-methyl-8-(4-methylpiperazin-1-yl)-1,2,3,4-tetrahydro-5H-chromeno[3,4-c]pyridin-5-one

[Formula 15]

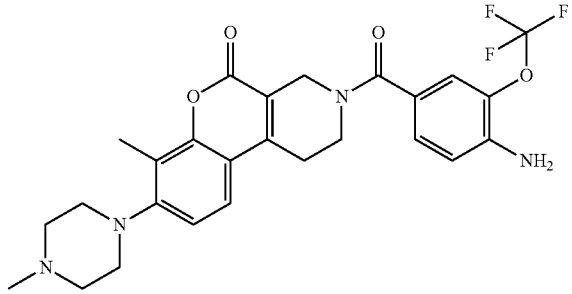

Using 7-methyl-8-(4-methylpiperazin-1-yl)-1,2,3,4-tetrahydrochromeno[3,4-c]pyridin-5-one dihydrochloride (100 mg) and 4-amino-3-(trifluoromethoxy)benzoic acid (63 mg), synthesis was carried out in the same manner as in Step 6 of Example 1 to obtain the title compound (126 mg) as a solid.

$^1$H-NMR (DMSO-D$_6$, 80° C.) δ: 2.28 (3H, s), 2.28 (3H, s), 2.52-2.57 (4H, m), 2.92-2.99 (6H, m), 3.78 (2H, t, J=5.8 Hz), 4.40 (2H, s), 5.63 (2H, s), 6.87 (1H, d, J=8.5 Hz), 7.07 (1H, d, J=8.5 Hz), 7.21-7.25 (2H, m), 7.51 (1H, d, J=8.5 Hz).

MS (ESI/APCI) m/z: 517 [M+H]+

[Step 2] N-[4-{[7-Methyl-8-(4-methylpiperazin-1-yl)-5-oxo-1,5-dihydro-2H-chromeno[3,4-c]pyridin-3(4H)-yl]carbonyl}-2-(trifluoromethoxy)phenyl]methanesulfonamide

[Formula 16]

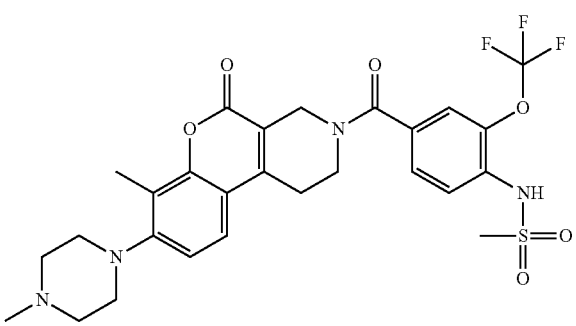

To a suspension of 3-[4-amino-3-(trifluoromethoxy)benzoyl]-7-methyl-8-(4-methylpiperazin-1-yl)-1,2,3,4-tetrahydro-5H-chromeno[3,4-c]pyridin-5-one (100 mg) in pyridine (2 ml), methanesulfonyl chloride (0.151 ml) was added. The reaction solution was stirred at 60° C. for 3 hours, cooled to room temperature and allowed to stand overnight. The reaction solution was concentrated under reduced pressure and tetrahydrofuran (2 ml), methanol (1 ml) and a 1 N aqueous solution of sodium hydroxide (3.8 ml) were added and the resultant reaction solution was stirred at room temperature for one hour. To the reaction solution, 1 N hydrochloric acid (0.95 ml) was added. The reaction solution was concentrated under reduced pressure and azeotropically distillated together with ethanol, sequentially purified by amino-silica gel chromatography (10-50% methanol/methylene chloride) and silica gel chromatography (2-14% methanol/methylene chloride). The resultant slurry was cleaned with diisopropyl ether to obtain the title compound (56 mg) as a solid.

$^1$H-NMR (DMSO-D$_6$, 80° C.) δ: 2.29 (3H, s), 2.29 (3H, s), 2.54-2.57 (4H, m), 2.93-2.99 (6H, m), 3.10 (3H, s), 3.74-3.80 (2H, m), 4.40 (2H, s), 7.06-7.09 (1H, m), 7.44-7.53 (3H, m), 7.61-7.65 (1H, m).

MS (ESI/APCI) m/z: 595 [M+H]+

Example 4

[Step 1] 3-(4-Amino-3-chlorobenzoyl)-8-[(3S)-3,4-dimethylpiperazin-1-yl]-7-methyl-1,2,3,4-tetrahydro-5H-chromeno[3,4-c]pyridin-5-one

[Formula 17]

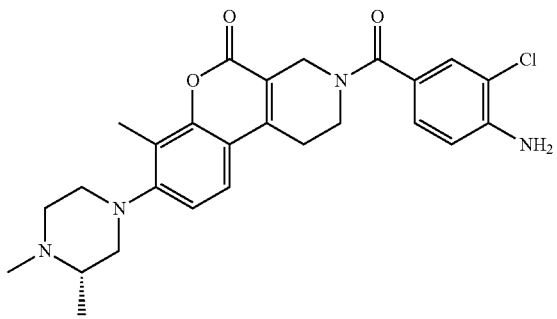

To a solution of tert-butyl 8-[(3S)-3,4-dimethylpiperazin-1-yl]-7-methyl-5-oxo-2,4-dihydro-1H-chromeno[3,4-c]pyridine-3-carboxylate (21 mg) in methanol (1 ml), a 4 N hydrochloric acid/1,4-dioxane (1 ml) was added. The reaction solution was stirred at room temperature for one hour, concentrated under reduced pressure and dried under vacuum to obtain a solid. The solid obtained, 4-amino-3-chlorobenzoic acid (10 mg), 1-ethyl-3-(3-dimethylaminopropyl)carbodiimide hydrochloride (12 mg) and 3H-1,2,3-triazolo[4,5-b]pyridin-3-ol (9 mg) were dissolved in anhydrous dichloromethane (1 ml) and N,N-diisopropylethylamine (0.033 ml) was added hereto. The resultant solution was stirred at room temperature for one day, allowed to stand, diluted with chloroform. A saturated aqueous solution of hydrogen carbonate was added and the resultant reaction solution was vigorously stirred. The organic layer was separated through a phase separator (Biotage), concentrated and then purified by silica gel chromatography (2-12% methanol/methylene chloride) to obtain the title compound (19 mg) as a solid.

MS (ESI/APCI) m/z: 481 [M+H]+
$^1$H-NMR (DMSO-D$_6$, 80° C.) δ: 1.04 (3H, d, J=6.1 Hz), 2.25 (3H, s), 2.29 (3H, s), 2.33-2.40 (1H, m), 2.51-2.56 (1H, m), 2.80-3.03 (7H, m), 3.77 (2H, t, J=5.8 Hz), 4.39 (2H, s), 5.60 (2H, s), 6.84 (1H, d, J=7.9 Hz), 7.05 (1H, d, J=8.5 Hz), 7.19 (1H, dd, J=8.5, 1.8 Hz), 7.34 (1H, d, J=1.8 Hz), 7.51 (1H, d, J=8.5 Hz).

[Step 2] N-[2-Chloro-4-({8-[(3S)-3,4-dimethylpiperazin-1-yl]-7-methyl-5-oxo-1,5-dihydro-2H-chromeno[3,4-c]pyridin-3(4H)-yl}carbonyl)phenyl]methanesulfonamide Using 3-(4-amino-3-chlorobenzoyl)-8-[(3S)-3,4-dimethylpiperazin-1-yl]-7-methyl-1,2,3,4-tetrahydro-5H-chromeno[3,4-c]pyridin-5-one (17 mg), synthesis was carried out in the same manner as in Step 7 of Example 1 to obtain the title compound (8 mg) as a solid.

MS (ESI/APCI) m/z: 559 [M+H]+
$^1$H-NMR (DMSO-D$_6$, 80° C.) δ: 1.05 (3H, d, J=6.1 Hz), 2.28 (3H, s), 2.29 (3H, s), 2.32-2.45 (1H, m), 2.51-2.59 (1H, m), 2.82-3.01 (7H, m), 3.09 (3H, s), 3.75-3.79 (2H, m), 4.40 (2H, s), 7.06 (1H, d, J=8.5 Hz), 7.41-7.45 (1H, m), 7.50-7.57 (2H, m), 7.59 (1H, d, J=1.8 Hz).

Example 5

[Step 1] tert-Butyl 8-[(3S)-3,4-dimethylpiperazin-1-yl]-7-methyl-5-oxo-1,5-dihydro-2H-chromeno[3,4-c]pyridine-3(4H)-carboxylate

[Formula 19]

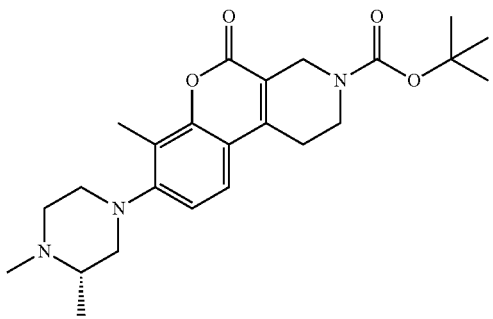

Using tert-butyl 7-methyl-5-oxo-8-{[(trifluoromethyl)sulfonyl]oxy}-1,5-dihydro-2H-chromeno[3,4-c]pyridine-3(4H)-carboxylate (723 mg) and (2S)-1,2-dimethylpiperazine dihydrochloride (583 mg), synthesis was carried out in the same manner as in Step 4 of Example 1 to obtain the title compound (507 mg) as a solid.

MS (ESI/APCI) m/z: 428 [M+H]+
$^1$H-NMR (CDCl$_3$) δ: 1.13 (3H, d, J=6.1 Hz), 1.50 (9H, s), 2.32-2.43 (7H, m), 2.47-2.64 (2H, m), 2.82-3.14 (6H, m), 3.70-3.75 (2H, m), 4.40 (2H, s), 6.98 (1H, d, J=8.5 Hz), 7.36 (1H, d, J=8.5 Hz).

[Step 2] 8-[(3S)-3,4-Dimethylpiperazin-1-yl]-7-methyl-1,2,3,4-tetrahydro-5H-chromeno[3,4-c]pyridin-5-one dihydrochloride

[Formula 18]

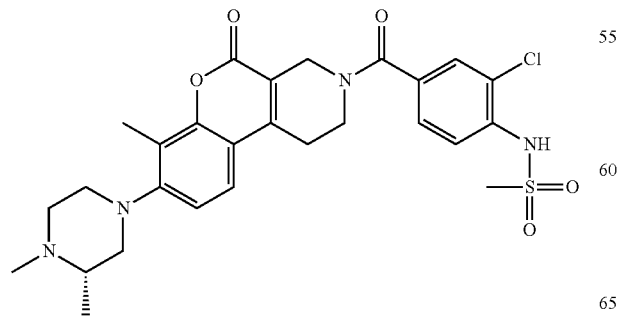

[Formula 20]

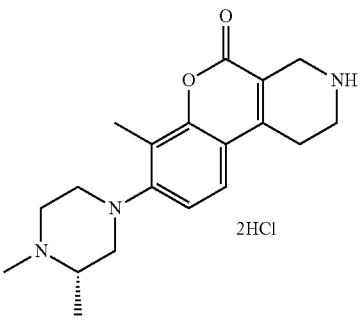

Using tert-butyl 8-[(3S)-3,4-dimethylpiperazin-1-yl]-7-methyl-5-oxo-1,5-dihydro-2H-chromeno[3,4-c]pyridine-3(4H)-carboxylate (505 mg), synthesis was carried out in the same manner as in Step 5 of Example 1 to obtain the title compound (496 mg) as a solid.

MS (ESI/APCI) m/z: 328 [M+H]+

$^1$H-NMR (DMSO-D$_6$) δ: 1.36 (3H, d, J=6.1 Hz), 2.32 (3H, s), 2.64-3.57 (14H, m), 3.96-4.01 (2H, m), 7.16 (1H, d, J=8.5 Hz), 7.63 (1H, d, J=8.5 Hz), 9.53 (2H, br s), 10.77 (1H, br s).

[Step 3] 3-[4-Amino-3-(trifluoromethoxy)benzoyl]-8-[(3S)-3,4-dimethylpiperazin-1-yl]-7-methyl-1,2,3,4-tetrahydro-5H-chromeno[3,4-c]pyridin-5-one

[Formula 21]

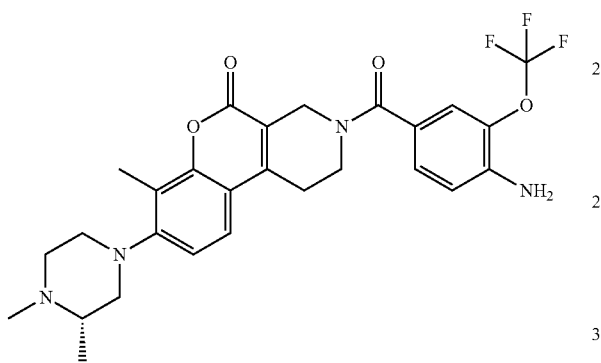

Using 8-[(3S)-3,4-dimethylpiperazin-1-yl]-7-methyl-1,2,3,4-tetrahydro-5H-chromeno[3,4-c]pyridin-5-one dihydrochloride (65 mg) and 4-amino-3-(trifluoromethoxy)benzoic acid (37 mg), synthesis was carried out in the same manner as in Step 6 of Example 1 to obtain the title compound (56 mg) as a solid.

$^1$H-NMR (DMSO-D$_6$, 80° C.) δ: 1.05 (3H, d, J=6.1 Hz), 2.26 (3H, s), 2.29 (3H, s), 2.47-2.61 (3H, m), 2.79-3.04 (6H, m), 3.74-3.81 (2H, m), 4.40 (2H, s), 5.62 (2H, s), 6.87 (1H, d, J=8.5 Hz), 7.05 (1H, d, J=8.5 Hz), 7.21-7.26 (2H, m), 7.51 (1H, d, J=9.1 Hz).

MS (ESI/APCI) m/z: 531 [M+H]+

[Step 4] N-[4-({8-[(3S)-3,4-Dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide

[Formula 22]

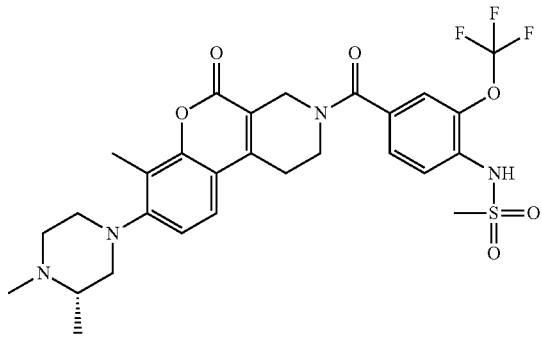

Using 3-[4-amino-3-(trifluoromethoxy)benzoyl]-8-[(3S)-3,4-dimethylpiperazin-1-yl]-7-methyl-1,2,3,4-tetrahydro-5H-chromeno[3,4-c]pyridin-5-one (55 mg) and methanesulfonyl chloride (0.029 ml), synthesis was carried out in the same manner as in Step 7 of Example 1 to obtain the title compound (57 mg) as a solid.

$^1$H-NMR (DMSO-D$_6$, 80° C.) δ: 1.06 (3H, d, J=6.1 Hz), 2.26-2.31 (6H, m), 2.34-2.59 (3H, m), 2.81-3.04 (6H, m), 3.10 (3H, s), 3.72-3.80 (2H, m), 4.40 (2H, s), 7.06 (1H, d, J=8.5 Hz), 7.44-7.53 (3H, m), 7.63 (1H, d, J=8.5 Hz).

MS (ESI/APCI) m/z: 609 [M+H]+

Example 6

[Step 1] 3-[4-Amino-3-(trifluoromethyl)benzoyl]-8-[(3S)-3,4-dimethylpiperazin-1-yl]-7-methyl-1,2,3,4-tetrahydro-5H-chromeno[3,4-c]pyridin-5-one

[Formula 23]

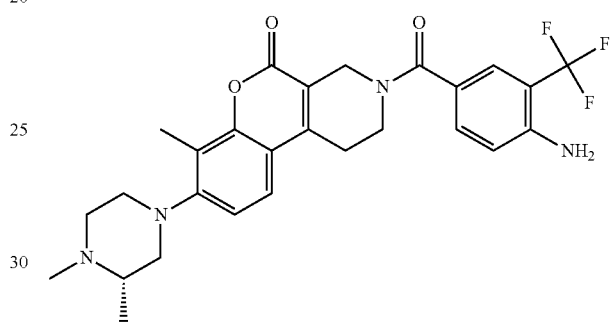

Using 8-[(3S)-3,4-dimethylpiperazin-1-yl]-7-methyl-1,2,3,4-tetrahydro-5H-chromeno[3,4-c]pyridin-5-one dihydrochloride (58 mg) and 4-amino-3-(trifluoromethyl)benzoic acid (33 mg), synthesis was carried out in the same manner as in Step 6 of Example 1 to obtain the title compound (63 mg) as a solid.

$^1$H-NMR (DMSO-D$_6$) δ: 7.54 (1H, d, J=8.5 Hz), 7.50-7.43 (2H, m), 7.06 (1H, d, J=8.5 Hz), 6.87 (1H, d, J=8.5 Hz), 6.14 (2H, s), 4.39 (2H, s), 3.76 (2H, s), 3.09-2.92 (4H, m), 2.89-2.81 (2H, m), 2.29-2.29 (1H, m), 2.27 (3H, s), 2.25 (3H, s), 1.04 (3H, d, J=6.1 Hz).

MS (ESI/APCI) m/z: 515 [M+1]+

[Step 2] N-[4-({8-[(3S)-3,4-Dimethylpiperazin-1-yl]-7-methyl-5-oxo-1,5-dihydro-2H-chromeno[3,4-c]pyridin-3(4H)-yl}carbonyl)-2-(trifluoromethyl)phenyl]methanesulfonamide

[Formula 24]

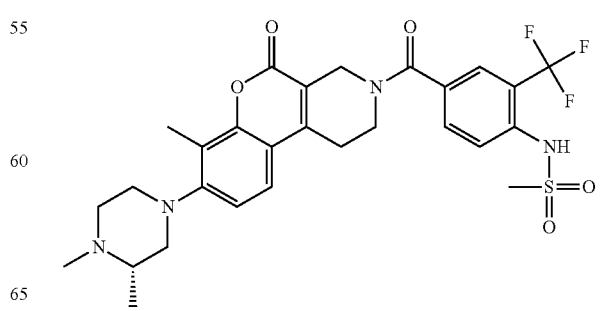

Using 3-[4-amino-3-(trifluoromethyl)benzoyl]-8-[(3S)-3,4-dimethylpiperazin-1-yl]-7-methyl-1,2,3,4-tetrahydro-5H-chromeno[3,4-c]pyridin-5-one (62 mg) and methanesulfonyl chloride (0.094 ml), synthesis was carried out in the same manner as in Step 7 of Example 1 to obtain the title compound (10 mg) as a solid.

$^1$H-NMR (DMSO-D$_6$) δ: 9.59 (1H, s), 7.72-7.61 (2H, m), 7.56 (2H, d, J=7.9 Hz), 7.10 (1H, d, J=8.5 Hz), 4.41 (2H, s), 3.77 (2H, br s), 3.20-3.10 (3H, m), 3.01-2.89 (6H, m), 2.85-2.74 (2H, m), 2.70-2.62 (2H, m), 2.30 (3H, s), 1.17 (3H, d, J=6.1 Hz).

MS (ESI/APCI) m/z: 593 [M+H]+

Example 7

[Step 1] 8-Hydroxy-7,10-dimethyl-1,2,3,4-tetrahydro-5H-chromeno[3,4-c]pyridin-5-one 1/2 sulfate

[Formula 25]

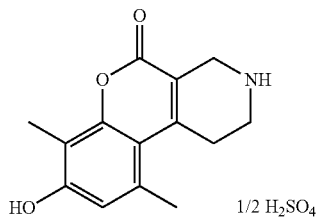

To ethyl 4-oxo-3-piperidinecarboxylate hydrochloride (3.11 g) and 2,5-dimethylresorcinol (2.07 g), 80% diluted sulfuric acid (50 g) was added little by little. The reaction solution was allowed to stand at room temperature for 3 days. The reaction solution was ice-cooled and ice (80 g) was added to the solution. The reaction solution was stirred at 0° C. for 30 minutes. The solid precipitated was collected by filtration and washed with a small volume of water. Ethanol/ethyl acetate=1/1 (30 ml) was added and the resultant reaction solution was stirred. Insoluble solid was collected by filtration and dried under reduced pressure to obtain the title compound (1.549 g) as a solid.

$^1$H-NMR (DMSO-D$_6$) δ: 2.13 (3H, s), 2.60 (3H, s), 3.19-3.31 (4H, m), 3.98 (2H, s), 6.71 (1H, s), 9.01 (2H, br s), 10.42 (1H, s)

MS (ESI/APCI) m/z: 246 [M+H]+

[Step 2] tert-Butyl 8-hydroxy-7,10-dimethyl-5-oxo-1,5-dihydro-2H-chromeno[3,4-c]pyridine-3(4H)-carboxylate

[Formula 26]

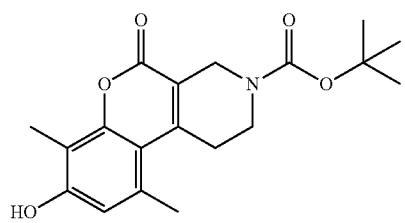

To a suspension of 8-hydroxy-7,10-dimethyl-1,2,3,4-tetrahydro-5H-chromeno[3,4-c]pyridin-5-one 1/2 sulfate (1.527 g) in water (11 ml) and a 1 N aqueous solution of sodium hydroxide (8.9 ml), a solution of di-tert-butyl dicarbonate (1.07 g) in tetrahydrofuran (20 ml) was added. The reaction solution was stirred at room temperature for 4 hours, diluted with water (30 ml), ice-cooled for about 20 minutes and filtered to obtain an insoluble solid. The insoluble solid was dried under reduced pressure to obtain the title compound (1.425 g) as a solid.

$^1$H-NMR (CDCl$_3$) δ: 1.51 (9H, s), 2.30 (3H, s), 2.62 (3H, s), 3.01-3.11 (2H, m), 3.59-3.65 (2H, m), 4.40 (2H, s), 5.54 (1H, br s), 6.60 (1H, s).

MS (ESI/APCI) m/z: 344 [M–H]–

[Step 3] tert-Butyl 7,10-dimethyl-5-oxo-8-{[(trifluoromethyl)sulfonyl]oxy}-1,5-dihydro-2H-chromeno[3,4-c]pyridine-3(4H)-carboxylate

[Formula 27]

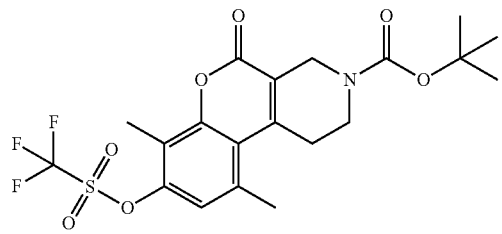

To a solution of tert-butyl 8-hydroxy-7,10-dimethyl-5-oxo-1,5-dihydro-2H-chromeno[3,4-c]pyridine-3(4H)-carboxylate (665 mg) in dichloromethane (25 ml), pyridine (0.280 ml) and trifluoromethanesulfonic anhydride (0.421 ml) were added dropwise under ice cooling. The reaction solution was stirred at 0° C. for 30 minutes and at room temperature for one hour. Again pyridine (0.280 ml) and trifluoromethanesulfonic anhydride (0.421 ml) were added dropwise to the reaction solution under ice-cooling. The reaction solution was stirred at room temperature for one hour. A saturated sodium bicarbonate water was added to the reaction solution and extracted with dichloromethane, dried over anhydrous sodium sulfate. After that, the solvent was evaporated under reduced pressure and the residue was purified by silica gel chromatography (1.5-3% methanol/methylene chloride) to obtain the title compound (425 mg) as a solid.

$^1$H-NMR (CDCl$_3$) δ: 1.51 (9H, s), 2.43 (3H, s), 2.72 (3H, s), 3.05-3.13 (2H, m), 3.61-3.67 (2H, m), 4.43 (2H, s), 7.01 (1H, s).

MS (ESI/APCI) m/z: 422 [M-tBu+H]+

[Step 4] tert-Butyl 8-[(3S)-3,4-dimethylpiperazin-1-yl]-7,10-dimethyl-5-oxo-1,5-dihydro-2H-chromeno[3,4-c]pyridine-3(4H)-carboxylate

[Formula 28]

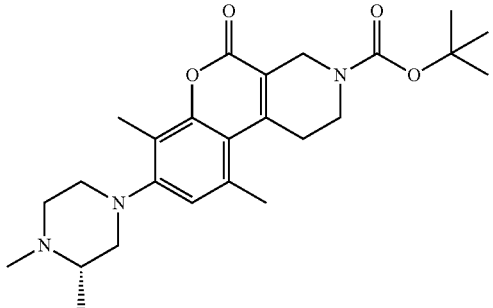

A suspension of tert-butyl 7,10-dimethyl-5-oxo-8-{[(trifluoromethyl) sulfonyl]oxy}-1,5-dihydro-2H-chromeno[3,4-c]pyridine-3(4H)-carboxylate (1.063 g), cesium carbonate (2.2 g), chloro-(2-dicyclohexylphosphino-2',6'-diisopropoxy-1,1'-biphenyl)[2-(2-aminoethyl)phenyl] palladium (II)-methyl-t-butyl ether adduct (91 mg), 2-dicyclohexylphosphino-2',6'-diisopropoxybiphenyl (52 mg), and (2S)-1,2-dimethylpiperazine (510 mg) in toluene (30 ml) was stirred while heating in a nitrogen atmosphere at 110° C. for 2.5 hours. The reaction solution was diluted with chloroform and a small volume of methanol and an insoluble solid was filtered off and the mother liquid was concentrated. The residue was purified by silica gel column chromatography (4-8% methanol/chloroform) to obtain the title compound (710 mg) as a solid.

$^1$H-NMR (CDCl$_3$) δ: 1.13 (3H, d, J=6.1 Hz), 1.50 (9H, s), 2.29-2.40 (1H, m), 2.33 (3H, s), 2.37 (3H, s), 2.46-2.62 (2H, m), 2.66 (3H, s), 2.87-2.98 (2H, m), 2.99-3.14 (4H, m), 3.58-3.65 (2H, m), 4.40 (2H, s), 6.70 (1H, s).

MS (ESI/APCI) m/z: 442 [M+H]+

[Step 5] 8-[(3S)-3,4-Dimethylpiperazin-1-yl]-7,10-dimethyl-1,2,3,4-tetrahydro-5H-chromeno[3,4-c]pyridin-5-one dihydrochloride

[Formula 29]

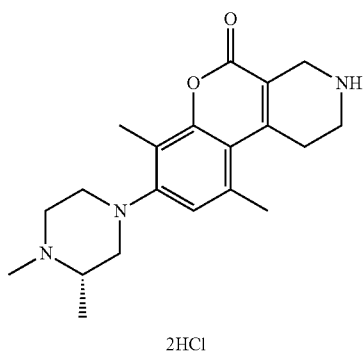

2HCl

To a solution of tert-butyl 8-[(3S)-3,4-dimethylpiperazin-1-yl]-7,10-dimethyl-5-oxo-1,5-dihydro-2H-chromeno[3,4-c]pyridine-3(4H)-carboxylate (693 mg) in methanol (10 ml), a 4 N hydrochloric acid/1,4-dioxane solution (10 ml) was added. The reaction solution was stirred at room temperature for one hour. The solvent was evaporated under reduced pressure. To the residue, a small volume of methanol was added to dissolve the residue. To this, ethyl acetate and diethyl ether were added, and the precipitated solid was collected by filtration and dried under reduced pressure to obtain the title compound (615 mg) as a solid.

$^1$H-NMR (DMSO-D$_6$, 80° C.) δ: 1.38 (3H, d, J=6.1 Hz), 2.27 (3H, s), 2.68 (3H, s), 2.82 (3H, s), 3.01-3.16 (1H, m), 3.22-3.38 (8H, m), 3.39-3.55 (2H, m), 3.98 (2H, s), 6.92 (1H, s), 9.52 (1H, br s).

MS (ESI/APCI) m/z: 342 [M+H]+

[Step 6] N-[2-Chloro-4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)phenyl] methanesulfonamide

[Formula 30]

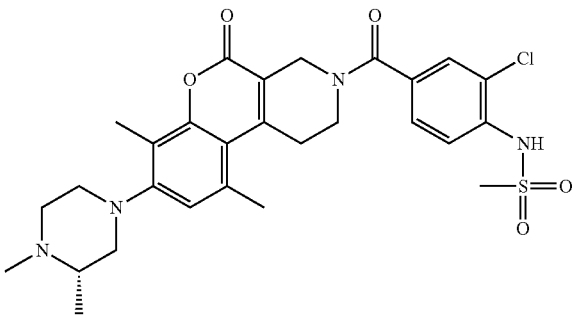

To a solution of 8-[(3S)-3,4-dimethylpiperazin-1-yl]-7,10-dimethyl-1,2,3,4-tetrahydro-5H-chromeno[3,4-c]pyridin-5-one dihydrochloride (42 mg), 3-chloro-4-[(methylsulfonyl)amino] benzoic acid (28 mg) and 3H-1,2,3-triazolo[4,5-b] pyridin-3-ol (16 mg) in N,N-dimethylformamide (3 ml), 1-ethyl-3-(3-dimethylaminopropyl)carbodiimide hydrochloride (22 mg) and N,N-diisopropylethylamine (0.11 ml) were added. The reaction solution was stirred at room temperature and allowed to stand for 4 days. The solvent was evaporated under reduced pressure and the residue was purified by silica gel column chromatography (5-12% methanol/methylene chloride) to obtain the title compound (22 mg) as a solid.

$^1$H-NMR (DMSO-D$_6$, 80° C.) δ: 9.57 (1H, brs), 7.64-7.54 (2H, m), 7.47 (1H, dd, J=8.2, 2.1 Hz), 6.85 (1H, s), 4.40 (2H, s), 3.67 (2H, s), 3.22-2.98 (11H, m), 2.90-2.68 (2H, m), 2.67 (3H, s), 2.55-2.50 (2H, m), 2.25 (3H, s), 1.19 (3H, d, J=5.5 Hz).

MS (ESI/APCI) m/z: 573 [M+1]+

Example 8

[Step 1] 4-[(Methylsulfonyl)amino]-3-(trifluoromethoxy)benzoic acid

[Formula 31]

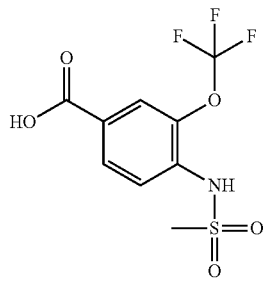

To a solution of methyl 4-amino-3-(trifluoromethoxy) benzoate (600 mg) in chloroform (20 ml), triethylamine (2.12 ml) and methanesulfonyl chloride (0.795 ml) were added dropwise under ice-cooling. The reaction solution was stirred at 0° C. for 10 minutes and at room temperature for 2 hours. Saturated sodium bicarbonate water was added thereto, and the reaction solution was stirred at room temperature for 20 minutes and extracted with chloroform. The organic layer was dried over anhydrous sodium sulfate and the solvent was evaporated under reduced pressure. The residue was dissolved in methanol (20 ml). A 1 N aqueous solution of sodium hydroxide (20.4 ml) was added and the resultant reaction solution was stirred at 70° C. for one hour while heating. After the temperature of the solution was returned to room temperature and the reaction solution was concentrated up to about half under reduced pressure, 5 N hydrochloric acid (4 ml) was added dropwise. The precipitated solid was collected by filtration and dried under reduced pressure to obtain the title compound (740 mg) as a solid.

$^1$H-NMR (DMSO-D$_6$) δ: 3.17 (3H, s), 7.70 (1H, d, J=8.5 Hz), 7.81-7.84 (1H, m), 7.93 (1H, dd, J=8.9, 2.1 Hz), 10.25 (1H, s), 13.31 (1H, s).

MS (ESI/APCI) m/z: 298 [M−1]−

[Step 2] N-[4-({8-[(3S)-3,4-Dimethylpiperazin-1-yl]-7,10-dimethyl-5-oxo-1,5-dihydro-2H-chromeno[3,4-c]pyridin-3(4H)-yl}carbonyl)-2-(trifluoromethoxy)phenyl]methanesulfonamide

[Formula 32]

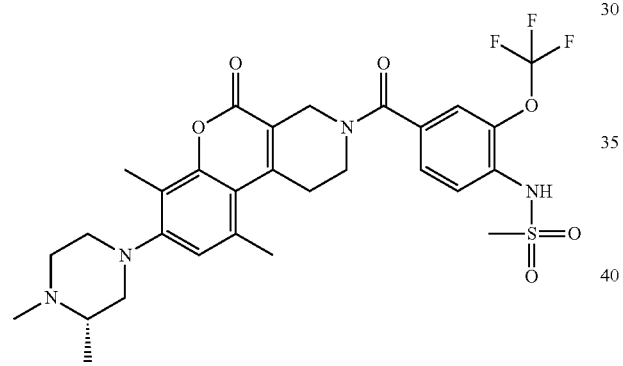

To a solution of 8-[(3S)-3,4-dimethylpiperazin-1-yl]-7,10-dimethyl-1,2,3,4-tetrahydro-5H-chromeno[3,4-c]pyridin-5-one dihydrochloride (45 mg), 4-[(methylsulfonyl)amino]-3-(trifluoromethoxy)benzoic acid (35 mg), 3H-1,2,3-triazolo[4,5-b]pyridin-3-ol (15 mg) and 1-ethyl-3-(3-dimethylaminopropyl)carbodiimide hydrochloride (23 mg) in N,N-dimethylformamide (3 ml), N,N-diisopropylethylamine (0.12 ml) was added. The reaction solution was stirred at room temperature and allowed to stand for 4 days. The solvent was evaporated under reduced pressure and the residue was purified by silica gel column chromatography (2-8% methanol/methylene chloride). To the solid obtained, ethyl acetate/hexane was added and insoluble matter was collected by filtration and dried at 60° C. for 2 hours under reduced pressure to obtain the title compound (29 mg) as a solid.

$^1$H-NMR (DMSO-D$_6$, 80° C.) δ: 9.69 (1H, s), 7.65 (1H, d, J=8.5 Hz), 7.52-7.47 (2H, m), 6.83 (1H, s), 4.41 (2H, s), 3.71-3.63 (2H, m), 3.22-3.17 (2H, m), 3.13-2.86 (9H, m), 2.66-2.52 (4H, m), 2.38 (3H, s), 2.24 (3H, s), 1.10 (3H, d, J=6.1 Hz).

MS (ESI/APCI) m/z: 623 [M+H]+

Example 9

[Step 1] 4-[(Ethylsulfonyl)amino]-3-(trifluoromethoxy)benzoic acid

[Formula 33]

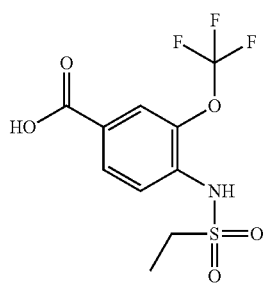

Using methyl 4-amino-3-(trifluoromethoxy)benzoate (300 mg) and ethanesulfonyl chloride (0.724 ml), synthesis was carried out in the same manner as in Step 1 of Example 8 to obtain the title compound (408 mg) as a solid.

$^1$H-NMR (DMSO-D$_6$) δ: 1.25 (3H, t, J=7.3 Hz), 3.27 (2H, q, J=7.3 Hz), 7.69 (1H, d, J=9.2 Hz), 7.80-7.84 (1H, m), 7.91 (1H, dd, J=8.5, 1.8 Hz), 10.27 (1H, s), 13.31 (1H, br s).

MS (ESI/APCI) m/z: 312 [M−H]−

[Step 2] N-[4-({8-[(3S)-3,4-Dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]ethanesulfonamide

[Formula 34]

Using 8-[(3S)-3,4-dimethylpiperazin-1-yl]-7-methyl-1,2,3,4-tetrahydro-5H-chromeno[3,4-c]pyridin-5-one dihydrochloride (55 mg) and 4-[(ethylsulfonyl)amino]-3-(trifluoromethoxy)benzoic acid (42 mg), synthesis was carried out in the same manner as in Step 2 of Example 8 to obtain the title compound (57 mg) as a solid.

$^1$H-NMR (DMSO-D$_6$, 80° C.) δ: 1.05 (3H, d, J=6.1 Hz), 1.29 (3H, t, J=7.3 Hz), 2.28 (3H, s), 2.29 (3H, s), 2.30-2.59 (3H, m), 2.82-3.04 (6H, m), 3.21 (2H, q, J=7.3 Hz), 3.72-3.80 (2H, m), 4.40 (2H, s), 7.06 (1H, d, J=8.5 Hz), 7.43-7.47 (2H, m), 7.51 (1H, d, J=8.5 Hz), 7.62 (1H, d, J=9.2 Hz), 9.66 (1H, br s).

MS (ESI/APCI) m/z: 623 [M+H]+

Example 10

N-[4-({8-[(3S)-3,4-Dimethylpiperazin-1-yl]-7,10-dimethyl-5-oxo-1,5-dihydro-2H-chromeno[3,4-c]pyridin-3(4H)-yl}carbonyl)-2-(trifluoromethoxy)phenyl]ethanesulfonamide

[Formula 35]

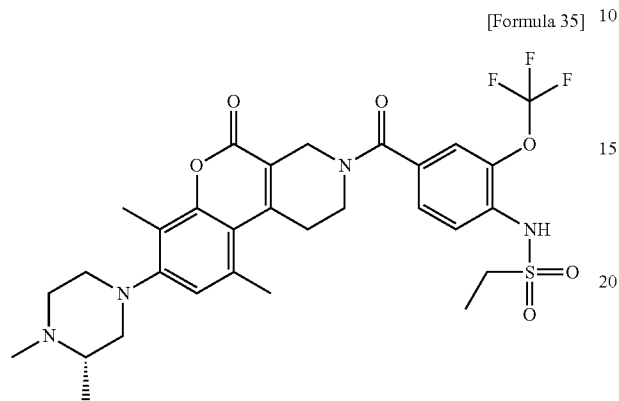

Using 8-[(3S)-3,4-dimethylpiperazin-1-yl]-7,10-dimethyl-1,2,3,4-tetrahydro-5H-chromeno[3,4-c]pyridin-5-one dihydrochloride (67 mg) and 4-[(ethylsulfonyl)amino]-3-(trifluoromethoxy)benzoic acid (49 mg), synthesis was carried out in the same manner as in Step 2 of Example 8 to obtain the title compound (71 mg) as a solid.

$^1$H-NMR (DMSO-D$_6$, 80° C.) δ: 1.05 (3H, d, J=6.1 Hz), 1.29 (3H, t, J=7.3 Hz), 2.23 (3H, s), 2.28 (3H, s), 2.29-2.45 (3H, m), 2.51-2.58 (1H, m), 2.65 (3H, s), 2.81-2.92 (2H, m), 2.98-3.04 (1H, m), 3.15-3.24 (4H, m), 3.64-3.71 (2H, m), 4.40 (2H, s), 6.82 (1H, s), 7.45-7.50 (2H, m), 7.63 (1H, d, J=8.5 Hz), 9.66 (1H, br s).

MS (ESI/APCI) m/z: 637[M+H]+

Example 11

[Step 1] tert-Butyl (3S)-3-ethyl-4-methylpiperazine-1-carboxylate

[Formula 36]

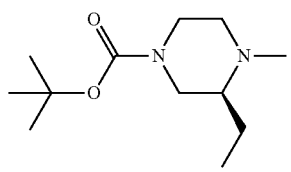

To a solution of tert-butyl (3S)-3-ethyl piperazine-1-carboxylate (2.0 g) in dichloromethane (20 ml), a 37% aqueous solution of formalin (3.4 ml) was added at room temperature. The reaction solution was ice-cooled and sodium triacetoxyborohydride (3.0 g) was added thereto. After that, the temperature of the reaction solution was gradually returned to room temperature and the reaction solution was stirred for 4 hours. To the reaction solution, a 1 N aqueous solution of sodium hydroxide (50 ml) was added. The reaction solution was stirred and dichloromethane and water were added, and the layers were separated. The organic layer was dried over anhydrous sodium sulfate, filtered and concentrated. The residue was purified by silica gel column chromatography (0-10% methanol/dichloromethane) to obtain the title compound (2.14 g) as an oily substance.

$^1$H-NMR (CDCl$_3$) δ: 4.04-3.69 (2H, m), 3.05 (1H, t, J=11.0 Hz), 2.90-2.53 (2H, m), 2.29 (3H, s), 2.24-2.13 (1H, m), 1.94-1.85 (1H, m), 1.74-1.62 (1H, m), 1.49-1.30 (10H, m), 0.92 (3H, t, J=7.9 Hz).

MS (ESI/APCI) m/z: 229 [M+H]+

[Step 2] (2S)-2-Ethyl-1-methylpiperazine dihydrochloride

[Formula 37]

To a solution of tert-butyl (3S)-3-ethyl-4-methylpiperazine-1-carboxylate (2.14 g) in methanol (20 ml), 4 N hydrochloric acid/1,4-dioxane (20 ml) was added. The reaction solution was stirred at room temperature for 2 hours, then allowed to stand overnight, concentrated under reduced pressure and dried under reduced pressure at 60° C. to obtain the title compound (1.86 g) as a solid.

MS (ESI/APCI) m/z: 129 [M+H]+

[Step 3] tert-Butyl 8-[(3S)-3-ethyl-4-methylpiperazin-1-yl]-7-methyl-5-oxo-1,5-dihydro-2H-chromeno[3,4-c]pyridine-3(4H)-carboxylate

[Formula 38]

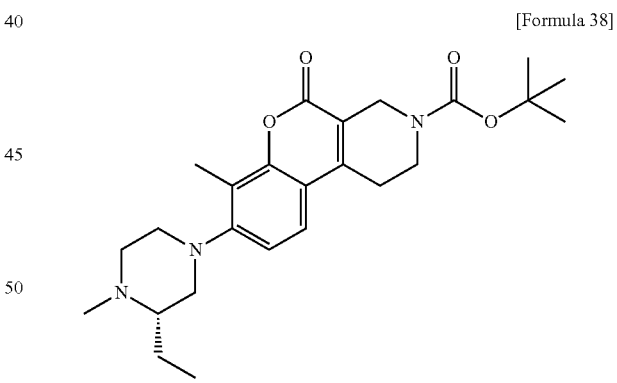

Using tert-butyl 7-methyl-5-oxo-8-{[(trifluoromethyl)sulfonyl]oxy}-1,5-dihydro-2H-chromeno[3,4-c]pyridine-3(4H)-carboxylate (1.5 g) and (2S)-2-ethyl-1-methylpiperazine dihydrochloride (1000 mg), synthesis was carried out in the same manner as in Step 4 of Example 1 to obtain the title compound (1.16 mg) as a solid.

$^1$H-NMR (CDCl$_3$) δ: 7.36 (1H, d, J=8.5 Hz), 6.98 (1H, d, J=8.5 Hz), 4.40 (2H, s), 3.73 (2H, t, J=5.8 Hz), 3.18-3.05 (2H, m), 3.00-2.82 (4H, m), 2.64-2.47 (2H, m), 2.38 (3H, s), 2.37 (3H, s), 2.23-2.15 (1H, m), 1.80-1.69 (1H, m), 1.51-1.39 (10H, m), 0.93 (3H, t, J=7.6 Hz).

MS (ESI & APCI) m/z: 442 [M+H]+

35

[Step 4] 8-[(3S)-3-Ethyl-4-methylpiperazin-1-yl]-7-methyl-1,2,3,4-tetrahydro-5H-chromeno[3,4-c]pyridin-5-one dihydrochloride

[Formula 39]

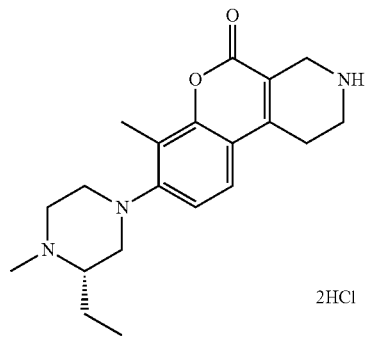

2HCl

Using tert-butyl 8-[(3S)-3-ethyl-4-methylpiperazin-1-yl]-7-methyl-5-oxo-1,5-dihydro-2H-chromeno[3,4-c]pyridine-3(4H)-carboxylate (1.16 g), synthesis was carried out in the same manner as in Step 5 of Example 1 to obtain the title compound (1.16 g) as a solid.

$^1$H-NMR (DMSO-D$_6$) δ: 10.83 (1H, s), 9.61 (2H, s), 7.64 (1H, d, J=8.5 Hz), 7.19 (1H, d, J=8.5 Hz), 3.99 (2H, s), 3.57-2.78 (12H, m), 2.32 (3H, s), 2.04-1.94 (1H, m), 1.71-1.58 (1H, m), 0.97 (3H, t, J=7.3 Hz).

MS (ESI/APCI) m/z: 342 [M+H]+

[Step 5] N-[4-({8-[(3S)-3-Ethyl-4-methylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide

[Formula 40]

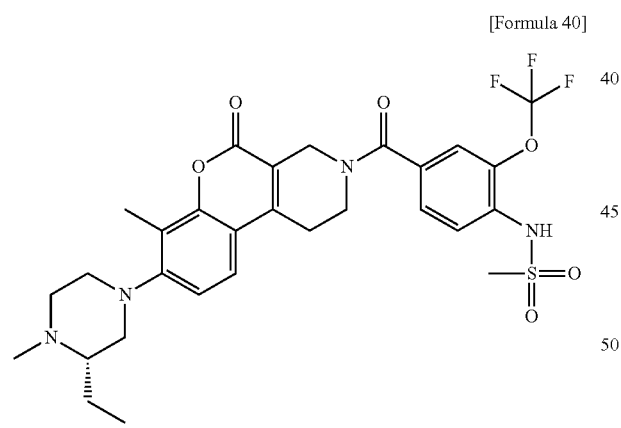

Using 8-[(3S)-3-ethyl-4-methylpiperazin-1-yl]-7-methyl-1,2,3,4-tetrahydro-5H-chromeno[3,4-c]pyridin-5-one dihydrochloride (50 mg) and 4-[(methylsulfonyl)amino]-3-(trifluoromethoxy)benzoic acid (35 mg), synthesis was carried out in the same manner as in Step 2 of Example 8 to obtain the title compound (53 mg) as a solid.

$^1$H-NMR (DMSO-D$_6$) δ: 10.02 (1H, s), 7.63 (1H, d, J=8.5 Hz), 7.56-7.46 (3H, m), 7.09 (1H, d, J=8.5 Hz), 4.41 (2H, s), 3.14-2.80 (9H, m), 2.59 (1H, t, J=10.9 Hz), 2.47-2.39 (1H, m), 2.36-2.17 (9H, m), 1.71-1.61 (1H, m), 1.48-1.37 (1H, m), 0.87 (3H, t, J=7.6 Hz).

MS (ESI/APCI) m/z: 623 [M+1]+

36

Example 12

[Step 1] tert-Butyl 7-methyl-5-oxo-8-(3,3,4-methylpiperazin-1-yl)-1,5-dihydro-2H-chromeno[3,4-c]pyridine-3(4H)-carboxylate

[Formula 41]

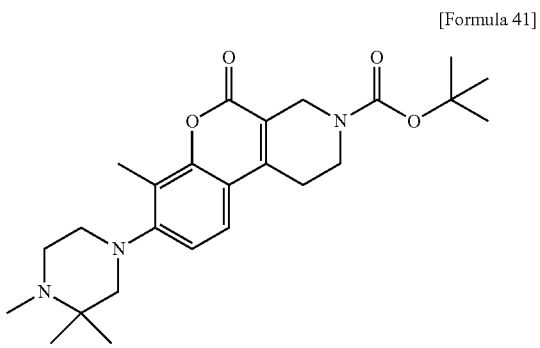 [SMILES: Cc1c(N2CCN(C)C(C)(C)C2)ccc2c3c(c(=O)oc12)CN(C(=O)OC(C)(C)C)CC3]

Using tert-butyl 7-methyl-5-oxo-8-{[(trifluoromethyl)sulfonyl]oxy}-1,5-dihydro-2H-chromeno[3,4-c]pyridine-3(4H)-carboxylate (500 mg) and 1,2,2-trimethylpiperazine dihydrochloride (260 mg), synthesis was carried out in the same manner as in Step 4 of Example 1 to obtain the title compound (350 mg) as a solid.

$^1$H-NMR (CDCl$_3$) δ: 7.36 (1H, d, J=8.5 Hz), 6.99 (1H, d, J=8.5 Hz), 4.40 (2H, s), 3.72 (2H, t, J=5.8 Hz), 3.05-2.98 (2H, m), 2.88-2.82 (2H, m), 2.80-2.73 (4H, m), 2.41 (3H, s), 2.33 (3H, s), 1.49 (9H, s), 1.18 (6H, s).

MS (ESI/APCI) m/z: 442 [M+H]+

[Step 2] 7-Methyl-8-(3,3,4-trimethylpiperazin-1-yl)-1,2,3,4-tetrahydro-5H-chromeno[3,4-c]pyridin-5-one dihydrochloride

[Formula 42]

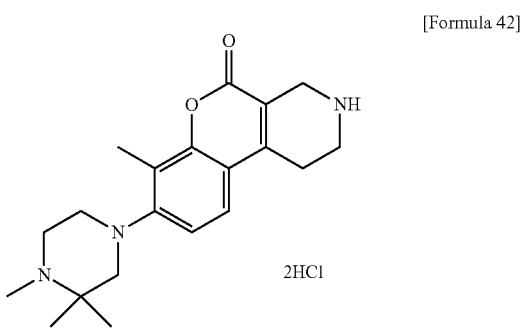 [SMILES: Cc1c(N2CCN(C)C(C)(C)C2)ccc2c3c(c(=O)oc12)CNCC3]

2HCl

Using tert-butyl 7-methyl-5-oxo-8-(3,3,4-methylpiperazin-1-yl)-1,5-dihydro-2H-chromeno[3,4-c]pyridine-3(4H)-carboxylate (350 mg), synthesis was carried out in the same manner as in Step 5 of Example 1 to obtain the title compound (313 mg) as a solid.

MS (ESI/APCI) m/z: 342[M+H]+

$^1$H-NMR (DMSO-D$_6$) δ: 9.59 (2H, s), 7.64 (1H, d, J=9.2 Hz), 7.16 (1H, d, J=9.2 Hz), 4.02-3.95 (2H, m), 3.54-3.03 (10H, m), 2.71 (3H, d, J=4.9 Hz), 2.35 (3H, s), 1.47 (3H, s), 1.43 (3H, s).

[Step 3] N-[4-{[7-Methyl-5-oxo-8-(3,3,4-trimethyl-piperazin-1-yl)-1,5-dihydro-2H-chromeno[3,4-c]pyridin-3(4H)-yl]carbonyl}-2-(trifluoromethoxy)phenyl]methanesulfonamide

[Formula 43]

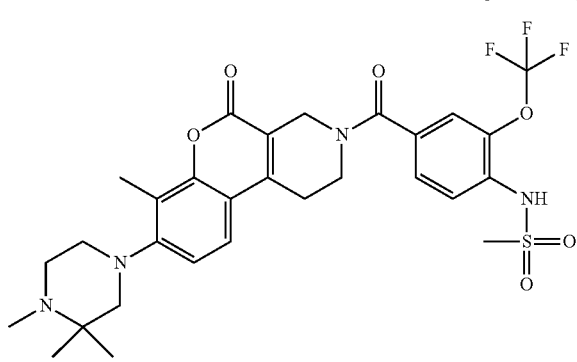

Using 7-methyl-8-(3,3,4-trimethylpiperazin-1-yl)-1,2,3,4-tetrahydro-5H-chromeno[3,4-c]pyridin-5-one dihydrochloride (60 mg) and 4-[(methylsulfonyl)amino]-3-(trifluoromethoxy)benzoic acid (43 mg), synthesis was carried out in the same manner as in Step 2 of Example 8 to obtain the title compound (67 mg) as a solid.

$^1$H-NMR (DMSO-D$_6$) δ: 10.01 (1H, s), 7.63 (1H, d, J=9.2 Hz), 7.58-7.48 (3H, m), 7.09 (1H, d, J=9.2 Hz), 4.41 (2H, s), 3.9-3.6 (2H, m), 3.11 (3H, s), 3.01-2.95 (4H, m), 2.83-2.72 (4H, m), 2.32 (6H, s), 1.15 (6H, s).

MS (ESI/APCI) m/z: 623 [M+H]+

Example 13

[Step 1] Benzyl 8-hydroxy-7-methyl-5-oxo-1,5-dihydro-2H-chromeno[3,4-c]pyridine-3(4H)-carboxylate

[Formula 44]

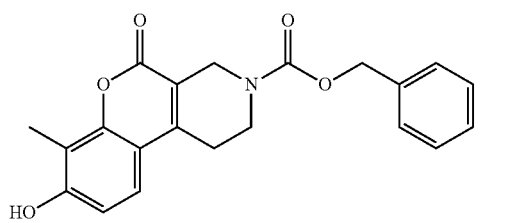

To a mixed suspension of 8-hydroxy-7-methyl-1,2,3,4-tetrahydro-5H-chromeno[3,4-c]pyridin-5-one 1/2 sulfate (10.0 g) in 1,4-dioxane (40 ml), water (26 ml) and a 5 N aqueous solution of sodium hydroxide (14 ml), benzyl chloroformate (5.58 ml) was added. The reaction solution was stirred at room temperature, then allowed to stand for 4 days and diluted with water. An insoluble solid was collected by filtration and dried under reduced pressure to obtain the title compound (12.69 g) as a solid.

$^1$H-NMR (DMSO-D$_6$, 80° C.) δ: 2.18 (3H, s), 2.81-2.89 (2H, m), 3.65-3.75 (2H, m), 4.21-4.31 (2H, m), 5.07-5.17 (2H, m), 6.82-6.89 (1H, m), 7.24-7.45 (6H, m).

MS (ESI/APCI) m/z: 366 [M+H]+

[Step 2] Benzyl 7-methyl-5-oxo-8-{[(trifluoromethyl)sulfonyl]oxy}-1,5-dihydro-2H-chromeno[3,4-c]pyridine-3(4H)-carboxylate

[Formula 45]

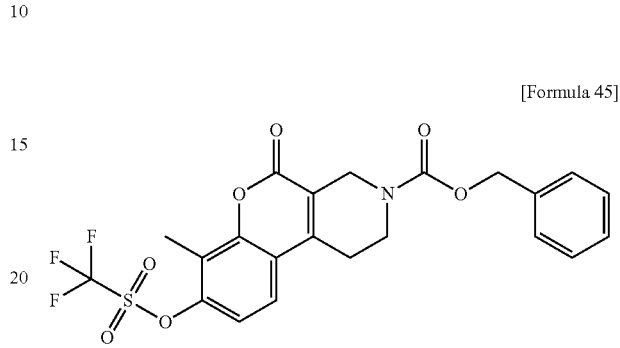

Using benzyl 8-hydroxy-7-methyl-5-oxo-1,5-dihydro-2H-chromeno[3,4-c]pyridine-3(4H)-carboxylate (12.63 g) and trifluoromethanesulfonic anhydride (9.35 ml), synthesis was carried out in the same manner as in Step 3 of Example 1 to obtain the title compound (13.91 g) as a solid.

$^1$H-NMR (DMSO-D$_6$, 80° C.) δ: 2.38 (3H, s), 2.90-2.97 (2H, m), 3.70-3.77 (2H, m), 4.33-4.38 (2H, m), 5.15 (2H, s), 7.28-7.46 (6H, m), 7.75 (1H, d, J=9.2 Hz).

MS (ESI/APCI) m/z: 498 [M+1]+

[Step 3] Benzyl 8-[(3S)-4-(tert-butoxycarbonyl)-3-methylpiperazin-1-yl]-7-methyl-5-oxo-1,5-dihydro-2H-chromeno[3,4-c]pyridine-3(4H)-carboxylate

[Formula 46]

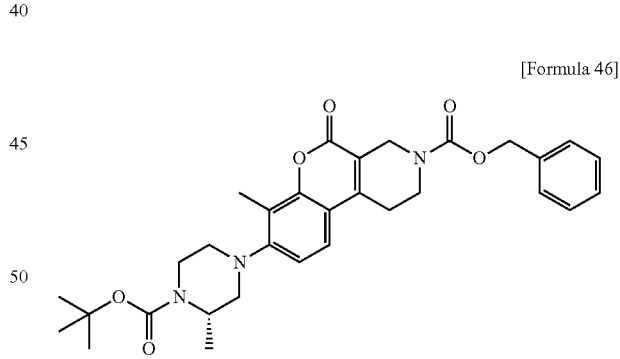

Using benzyl 7-methyl-5-oxo-8-{[(trifluoromethyl)sulfonyl]oxy}-1,5-dihydro-2H-chromeno[3,4-c]pyridine-3(4H)-carboxylate (500 mg) and tert-butyl (2S)-2-methylpiperazine-1-carboxylate (215 mg), synthesis was carried out in the same manner as in Step 4 of Example 1 to obtain the title compound (312 mg) as a solid.

$^1$H-NMR (DMSO-D$_6$) δ: 7.60-7.29 (6H, m), 7.08 (1H, d, J=8.5 Hz), 5.14 (2H, s), 4.36-4.19 (3H, m), 3.86-3.64 (3H, m), 3.22 (1H, t, J=11.9 Hz), 3.14-3.02 (2H, m), 2.94-2.87 (2H, m), 2.83-2.77 (1H, m), 2.72-2.63 (1H, m), 2.33 (3H, s), 1.43 (9H, s), 1.32 (3H, d, J=6.7 Hz).

MS (ESI/APCI) m/z: 548 [M+H]+

[Step 4] tert-Butyl (2S)-2-methyl-4-(7-methyl-5-oxo-1,3,4,5-tetrahydro-2H-chromeno[3,4-c]pyridine-8-yl) piperazine-1-carboxylate

[Formula 47]

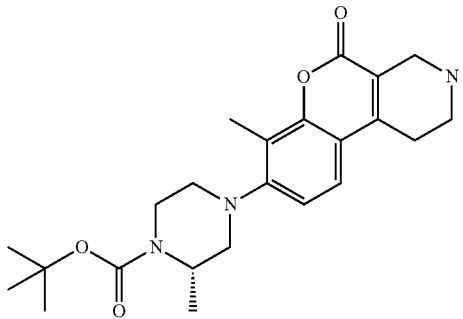

To a solution of benzyl 8-[(3S)-4-(tert-butoxycarbonyl)-3-methylpiperazin-1-yl]-7-methyl-5-oxo-1,5-dihydro-2H-chromeno[3,4-c]pyridine-3(4H)-carboxylate (312 mg) in methanol (10 ml), 10% palladium carbon (100 mg) was added. The reaction solution was stirred under a hydrogen atmosphere at room temperature for 4 hours and filtered. The solvent was evaporated to obtain the title compound (221 mg) as a solid.

$^1$H-NMR (CDCl$_3$) δ: 7.37 (1H, d, J=8.5 Hz), 6.95 (1H, d, J=8.5 Hz), 4.37 (1H, s), 4.01-3.93 (1H, m), 3.85 (2H, s), 3.37-3.26 (1H, m), 3.18 (2H, t, J=5.5 Hz), 3.12-3.06 (1H, m), 3.01-2.87 (2H, m), 2.81-2.69 (3H, m), 2.43 (3H, s), 1.49 (9H, s), 1.41 (3H, d, J=6.7 Hz).

MS (ESI/APCI) m/z: 414 [M+H]+

[Step 5] tert-Butyl (2S)-2-methyl-4-(7-methyl-3-{4-[(methylsulfonyl)amino]-3-(trifluoromethoxy)benzoyl}-5-oxo-1,3,4,5-tetrahydro-2H-chromeno[3,4-c]pyridine-8-yl) piperazine-1-carboxylate

[Formula 48]

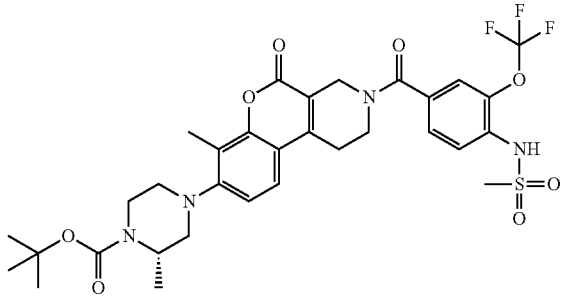

Using tert-butyl (2S)-2-methyl-4-(7-methyl-5-oxo-1,3,4,5-tetrahydro-2H-chromeno[3,4-c]pyridine-8-yl) piperazine-1-carboxylate (60 mg) and 4-[(methylsulfonyl)amino]-3-(trifluoromethoxy)benzoic acid (43 mg), synthesis was carried out in the same manner as in Step 2 of Example 8 to obtain the title compound (41 mg) as a solid.

$^1$H-NMR (CDCl$_3$) δ: 7.80 (1H, d, J=8.5 Hz), 7.50-7.35 (3H, m), 6.98 (1H, d, J=8.5 Hz), 6.86 (1H, s), 4.55-4.33 (2H, m), 4.09-3.94 (2H, m), 3.38-3.27 (1H, m), 3.13-3.06 (4H, m), 3.03-2.89 (4H, m), 2.80-2.72 (1H, m), 2.42 (3H, s), 1.53 (1H, d, J=1.2 Hz), 1.49 (9H, s), 1.40 (3H, d, J=6.7 Hz).

MS (ESI/APCI) m/z: 695 [M+1]+

[Step 6] N-[4-({7-Methyl-8-[(3S)-3-methylpiperazin-1-yl]-5-oxo-1,5-dihydro-2H-chromeno[3,4-c]pyridin-3(4H)-yl}carbonyl)-2-(trifluoromethoxy)phenyl]methanesulfonamide hydrochloride

[Formula 49]

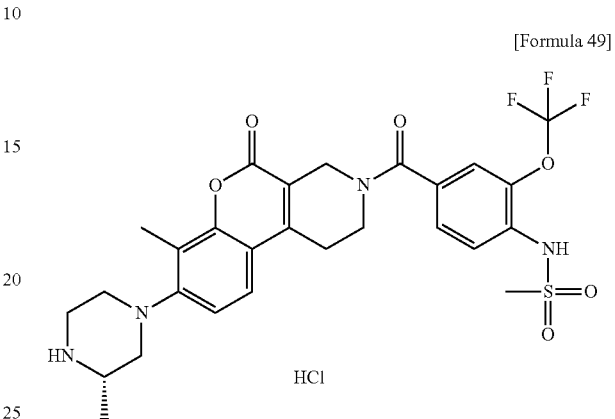

To a solution of tert-butyl (2S)-2-methyl-4-(7-methyl-3-{4-[(methylsulfonyl)amino]-3-(trifluoromethoxy)benzoyl}-5-oxo-1,3,4,5-tetrahydro-2H-chromeno[3,4-c]pyridine-8-yl) piperazine-1-carboxylate (40 mg) in methanol (5 ml), 4 N hydrochloric acid/1,4-dioxane (5 ml) was added. The reaction solution was stirred at room temperature for 2 hours, allowed to stand overnight and concentrated under reduced pressure. To the reaction solution, ethyl acetate was added and insoluble matter was collected by filtration and dried at 60° C. under reduced pressure to obtain the title compound (18 mg) as a solid.

$^1$H-NMR (DMSO-D$_6$) δ: 10.09 (1H, s), 9.30 (1H, d, J=10.0 Hz), 8.97 (1H, d, J=7.9 Hz), 7.66 (1H, d, J=8.5 Hz), 7.63-7.48 (3H, m), 7.14 (1H, d, J=8.5 Hz), 4.54-4.27 (2H, m), 4.00-3.17 (7H, m), 3.15 (3H, s), 3.05-2.94 (3H, m), 2.84 (1H, t, J=11.3 Hz), 2.35-2.25 (3H, m), 1.30 (3H, d, J=6.7 Hz).

MS (ESI/APCI) m/z: 595 [M+H]+

Example 14

[Step 1] tert-Butyl 8-[(3R,5S)-3,5-dimethylpiperazin-1-yl]-7-methyl-5-oxo-1,5-dihydro-2H-chromeno[3,4-c]pyridine-3(4H)-carboxylate

[Formula 50]

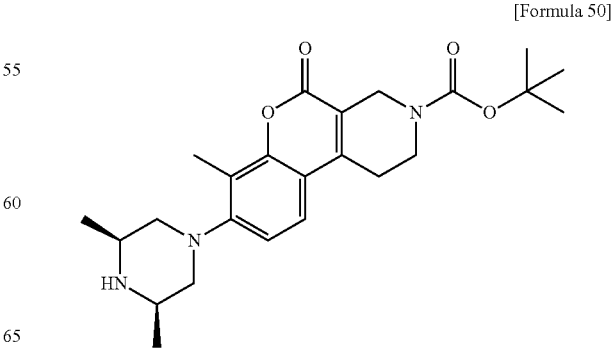

Using tert-butyl 7-methyl-5-oxo-8-(trifluoromethylsulfonyloxy)-2,4-dihydro-1H-chromeno[3,4-c]pyridine-3-carboxylate (499 mg) and (2R,6S)-2,6-dimethylpiperazine (370 mg), synthesis was carried out in the same manner as in Step 4 of Example 1 to obtain the title compound (111 mg) as a solid.

$^1$H-NMR (DMSO-D$_6$, 80° C.) δ: 1.00 (6H, d, J=6.1 Hz), 1.44 (9H, s), 2.23-2.31 (4H, m), 2.83-2.87 (2H, m), 2.95-3.04 (4H, m), 3.63 (2H, t, J=5.8 Hz), 4.22 (2H, s), 7.02 (1H, d, J=8.5 Hz), 7.49 (1H, d, J=8.5 Hz).

MS (ESI/APCI) m/z: 428 [M+H]+

[Step 2] tert-Butyl 7-methyl-5-oxo-8-[(3R,5S)-3,4,5-trimethylpiperazin-1-yl]-1,5-dihydro-2H-chromeno[3,4-c]pyridine-3(4H)-carboxylate

[Formula 51]

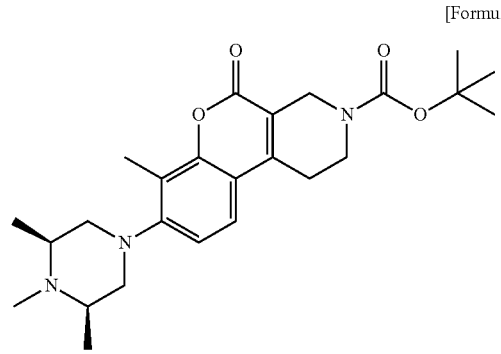

To a solution of tert-butyl 8-[(3R,5S)-3,5-dimethylpiperazin-1-yl]-7-methyl-5-oxo-1,5-dihydro-2H-chromeno[3,4-c]pyridine-3(4H)-carboxylate (99 mg) in dichloromethane (3 ml)-methanol (0.3 ml), a 37% aqueous solution of formaldehyde (0.0854 ml) was added. The reaction solution was stirred at room temperature for 20 minutes and ice-cooled. To the reaction solution, sodium triacetoxyborohydride (73 mg) was added. The reaction solution was stirred under ice cooling for 5 minutes and at room temperature for 50 minutes and diluted with dichloromethane. A saturated aqueous solution of sodium hydrogen carbonate was added and the resultant reaction solution was vigorously stirred at room temperature. The organic layer was separated through a phase separator (Biotage), concentrated and then purified by silica gel chromatography (2-10% methanol/methylene chloride) to obtain the title compound (86 mg) as a solid.

$^1$H-NMR (DMSO-D$_6$, 80° C.) δ: 1.05 (6H, d, J=6.1 Hz), 1.44 (9H, s), 2.24 (3H, s), 2.29 (3H, s), 2.35-2.41 (2H, m), 2.51-2.57 (2H, m), 2.83-2.87 (2H, m), 2.98-3.04 (2H, m), 3.63 (2H, t, J=5.8 Hz), 4.22 (2H, s), 7.02 (1H, d, J=8.5 Hz), 7.50 (1H, d, J=8.5 Hz).

MS (ESI/APCI) m/z: 442 [M+H]+

[Step 3] 7-Methyl-8-[(3R,5S)-3,4,5-trimethylpiperazin-1-yl]-1,2,3,4-tetrahydro-5H-chromeno[3,4-c]pyridin-5-one dihydrochloride

[Formula 52]

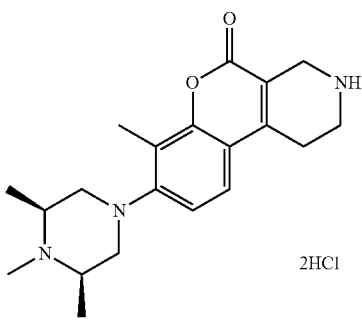

Using tert-butyl 7-methyl-5-oxo-8-[(3R,5S)-3,4,5-trimethylpiperazin-1-yl]-1,5-dihydro-2H-chromeno[3,4-c]pyridine-3(4H)-carboxylate (84 mg), synthesis was carried out in the same manner as in Step 5 of Example 1 to obtain the title compound as a solid.

MS (ESI/APCI) m/z: 342 [M+H]+

[Step 4] 3-(4-Amino-3-chlorobenzoyl)-7-methyl-8-[(3R,5S)-3,4,5-trimethylpiperazin-1-yl]-1,2,3,4-tetrahydro-5H-chromeno[3,4-c]pyridin-5-one

[Formula 53]

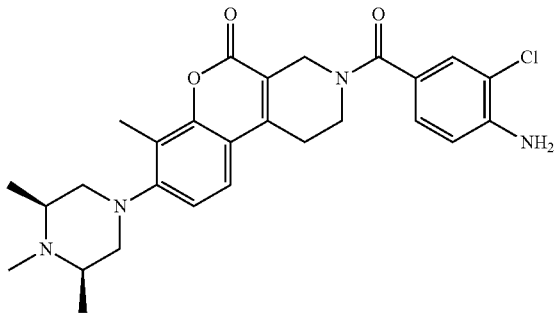

Using 7-methyl-8-[(3R,5S)-3,4,5-trimethylpiperazin-1-yl]-1,2,3,4-tetrahydro-5H-chromeno[3,4-c]pyridin-5-one dihydrochloride obtained in Step 3 of Example 14 and 4-amino-3-chlorobenzoic acid (39.7 mg), synthesis was carried out in the same manner as in Step 6 of Example 1 to obtain the title compound (79 mg) as a solid.

$^1$H-NMR (DMSO-D$_6$, 80° C.) δ: 1.05 (6H, d, J=6.1 Hz), 2.23 (3H, s), 2.28 (3H, s), 2.33-2.40 (2H, m), 2.54 (2H, t, J=10.9 Hz), 2.91-2.96 (2H, m), 2.99-3.07 (2H, m), 3.77 (2H, t, J=5.5 Hz), 4.39 (2H, s), 5.59 (2H, s), 6.84 (1H, d, J=8.5 Hz), 7.03 (1H, d, J=8.5 Hz), 7.16-7.21 (1H, m), 7.34 (1H, d, J=1.8 Hz), 7.50 (1H, d, J=9.1 Hz).

MS (ESI/APCI) m/z: 495 [M+H]+

[Step 5] N-[2-Chloro-4-({7-methyl-5-oxo-8-[(3R,5S)-3,4,5-trimethylpiperazin-1-yl]-1,5-dihydro-2H-chromeno[3,4-c]pyridin-3(4H)-yl}carbonyl)phenyl]methanesulfonamide

[Formula 54]

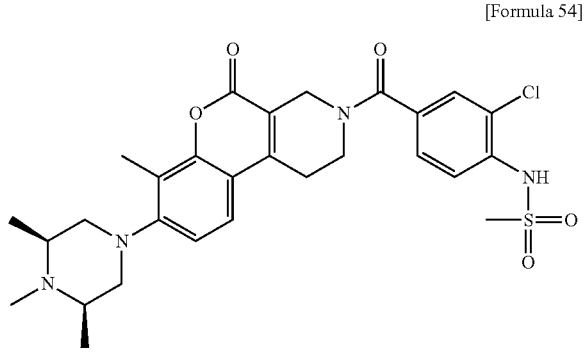 [SMILES: Cc1c(N2C[C@@H](C)N(C)[C@@H](C)C2)ccc2c3c(c(=O)oc12)CN(C(=O)c1ccc(NS(C)(=O)=O)c(Cl)c1)CC3]

To a solution of 3-(4-amino-3-chlorobenzoyl)-7-methyl-8-[(3R,5S)-3,4,5-trimethylpiperazin-1-yl]-1,2,3,4-tetrahydro-5H-chromeno[3,4-c]pyridin-5-one (79 mg) in pyridine (1.5 ml), methanesulfonyl chloride (0.0373 ml) was added. The reaction solution was stirred at 50° C. for 100 minutes. Methanesulfonyl chloride (0.0248 ml) was added and the resultant reaction solution was stirred for 30 minutes and cooled to room temperature. Pyridine (1 ml) and methanesulfonyl chloride (0.0373 ml) were added and the resultant solution was stirred at 55° C. for one hour, cooled to room temperature, concentrated under reduced pressure and stored in a refrigerator, overnight. The residue was diluted with chloroform and purified by silica gel column chromatography (2-15% methanol/methylene chloride). The residue obtained was dissolved in tetrahydrofuran (5 ml) and methanol (0.5 ml), and a 1 N aqueous solution of sodium hydroxide (0.318 ml) was added. The resultant reaction solution was stirred at room temperature for 50 minutes. To the reaction solution, 1 N hydrochloric acid (0.3 ml) was added. The reaction solution was concentrated under reduced pressure. The residue was purified with amino-silica gel chromatography (10-50% methanol/methylene chloride) and silica gel chromatography (1-12% methanol/methylene chloride). The concentrated residue (slurry) was washed with diisopropyl ether to obtain the title compound (37 mg) as a solid.

$^1$H-NMR (DMSO-D$_6$, 80° C.) δ: 1.07 (6H, d, J=5.5 Hz), 2.26 (3H, s), 2.29 (3H, s), 2.40-2.46 (2H, m), 2.52-2.60 (2H, m), 2.93-2.99 (2H, m), 3.00-3.07 (2H, m), 3.09 (3H, s), 3.74-3.79 (2H, m), 4.40 (2H, s), 7.02-7.06 (1H, m), 7.41-7.45 (1H, m), 7.49-7.53 (1H, m), 7.53-7.57 (1H, m), 7.58-7.61 (1H, m), 9.30 (1H, br s).

MS (ESI/APCI) m/z: 573 [M+H]+

Experimental Example

[MTHFD2 Dehydrogenase Assay]

To each of the wells of a 384-well plate (Greiner, 781801, UV transparent), a DMSO solution (4 μl) containing a test compound; 16 μl of a reaction buffer (0.1 M potassium phosphate (pH 7.3), 5 mM magnesium chloride, 0.01% Tween20) containing tetrahydrofolic acid (Schircks lab) and formaldehyde; and 20 μl of a reaction buffer (0.1 M potassium phosphate (pH 7.3), 5 mM magnesium chloride, 200 μM NAD, 0.01% Tween20) containing recombinant MTHFD2 protein; or 20 μl of a reaction buffer (0.1 M potassium phosphate (pH 7.3), 5 mM magnesium chloride, 0.01% Tween20) containing no MTHFD2 protein were added. The solution was mixed by centrifugation to initiate the reaction. After the reaction was carried out at room temperature for 30 minutes, a 1 M hydrochloric acid solution (10 μl) was added to terminate the reaction. After addition of the hydrochloric acid solution, the reaction solution was allowed to stand for 10 minutes or more. Then, the absorbance was measured at a wavelength of 355 nm, which is the absorption wavelength of methenyl-THF (a reaction product), by a microplate reader, SpectraMax Plus384. The value of the sample to which the solution containing no MTHFD2 protein was added was subtracted as the background value. Thereafter, the activity of the sample to which the DMSO solution containing no test compound was added was regarded as 100 and the 50% inhibitory concentration (IC50 value) was obtained.

[MTHFD1 Dehydrogenase Assay]

To each of the wells of a 384-well plate (Greiner, 781801, UV transparent), a DMSO solution (4 μl) containing a test compound; 16 μl of a reaction buffer (0.1 M potassium phosphate (pH 7.3), 5 mM magnesium chloride, 0.01% Tween20) containing tetrahydrofolic acid (Schircks lab) and formaldehyde; and 20 μl of a reaction buffer (0.1 M potassium phosphate (pH 7.3), 5 mM magnesium chloride, 165.4 μM NADP, 0.01% Tween20) containing recombinant MTHFD1 protein (dehydrogenase domain, alone); or 20 μl of a reaction buffer (0.1 M potassium phosphate (pH 7.3), 5 mM magnesium chloride, 0.01% Tween20) containing no MTHFD1 protein were added. The solution was mixed by centrifugation to initiate the reaction. After the reaction was carried out at room temperature for 30 minutes, a 1 M hydrochloric acid solution (10 μl) was added to terminate the reaction. After addition of the hydrochloric acid solution, the reaction solution was allowed to stand for 10 minutes or more. Then, the absorbance was measured at a wavelength of 355 nm, which is the absorption wavelength of methenyl-THF (a reaction product), by a microplate reader, SpectraMax Plus384. The value of the sample to which the solution containing no MTHFD1 protein was added was subtracted as the background value. Thereafter, the activity of the sample to which the DMSO solution containing no test compound was added was regarded as 100 and the 50% inhibitory concentration (IC50 value) was obtained.

[Growth Inhibition Test Using MDA-MB-231 Luc Cells]

MDA-MB-231 luc cells, which were obtained by introducing a luciferase gene into human breast cancer cell line, MDA-MB-231, were seeded in a 96 well plate at 2,000 cells/well. On the following day, a solution containing a test compound was added at 10 μl/well to initiate treatment with the compound. As the medium for the growth test, MEM, 10% dialyzed FBS, 400 μM Serine and 250 μM Glycine were used. On Day 3 after the treatment with the compound, 100 μl of a cell-titer Glo (Promega) solution diluted 2.5 times with PBS was added and the amount of luminescence was measured by EnVision. In order to evaluate the net effect on cell growth, the value on Day 0 was subtracted from the value on Day 3 after initiation of treatment with the compound. Based on the amount of growth by the sample containing no compound regarded as 100, the 50% inhibitory concentration (GI50 value) was obtained.

The MTHFD2 inhibitory activity, MTHFD1 inhibitory activity and cell growth inhibitory activity for the compounds of the Examples are shown in Table 1.

TABLE 1

| Example No. | MTHFD2 IC50 (µM) | MTHFD1 IC50 (µM) | GI50 (µM) |
| --- | --- | --- | --- |
| 1 | 0.048 | 6.4 | 0.94 |
| 2 | 0.028 | 2.2 | 1.1 |
| 3 | 0.021 | 2.9 | 0.38 |
| 4 | 0.0093 | 1.1 | 0.20 |
| 5 | 0.0063 | 0.57 | 0.14 |
| 6 | 0.0064 | 1.5 | 0.21 |
| 7 | 0.0044 | 0.56 | 0.10 |
| 8 | 0.0026 | 0.20 | 0.045 |
| 9 | 0.0047 | 0.40 | 0.12 |
| 10 | 0.0027 | 0.22 | 0.017 |
| 11 | 0.0051 | 0.36 | 0.12 |
| 12 | 0.075 | 0.71 | 0.066 |
| 13 | 0.0078 | 0.90 | 0.26 |
| 14 | 0.037 | 4.9 | 0.78 |

The invention claimed is:

1. A compound represented by formula (1):

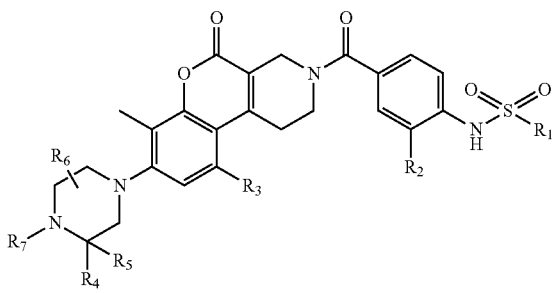

wherein,
- $R_1$ represents a $C_1$ to $C_6$ alkyl group or a $C_3$ to $C_6$ cycloalkyl group,
- $R_2$ represents a hydrogen atom, a halogen atom, a $C_1$ to $C_3$ alkyl group optionally substituted with 1 to 3 fluorine atoms or a $C_1$ to $C_3$ alkoxy group optionally substituted with 1 to 3 fluorine atoms,
- $R_3$ represents a hydrogen atom or a $C_1$ to $C_6$ alkyl group,
- $R_4$ represents a hydrogen atom or a $C_1$ to $C_6$ alkyl group,
- $R_5$ represents a hydrogen atom or a $C_1$ to $C_6$ alkyl group,
- $R_6$ represents a hydrogen atom or a $C_1$ to $C_6$ alkyl group, and
- $R_7$ represents a hydrogen atom or a $C_1$ to $C_6$ alkyl group, or a salt thereof.

2. The compound or a salt thereof according to claim 1, wherein the compound is any one selected from the group of:
   N-(2-chloro-4-{[7-methyl-8-(4-methylpiperazin-1-yl)-5-oxo-1,5-dihydro-2H-chromeno[3,4-c]pyridin-3(4H)-yl]carbonyl}phenyl)methanesulfonamide,
   N-(2-chloro-4-{[7-methyl-8-(4-methylpiperazin-1-yl)-5-oxo-1,5-dihydro-2H-chromeno[3,4-c]pyridin-3(4H)-yl]carbonyl}phenyl)cyclopropanesulfonamide,
   N-[4-{[7-methyl-8-(4-methylpiperazin-1-yl)-5-oxo-1,5-dihydro-2H-chromeno[3,4-c]pyridin-3(4H)-yl]carbonyl}-2-(trifluoromethoxy)phenyl]methanesulfonamide,
   N-[2-chloro-4-({8-[(3S)-3,4-dimethylpiperazin-1-yl]-7-methyl-5-oxo-1,5-dihydro-2H-chromeno[3,4-c]pyridin-3(4H)-yl}carbonyl)phenyl]methanesulfonamide,
   N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide,
   N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethyl)phenyl]methanesulfonamide,
   N-[2-chloro-4-({8-[(3S)-3,4-dimethylpiperazin-1-yl]-7,10-dimethyl-5-oxo-1,5-dihydro-2H-chromeno[3,4-c]pyridin-3(4H)-yl}carbonyl)phenyl]methanesulfonamide,
   N-[4-({8-[(3S)-3,4-dimethylpiperazin-1-yl]-'7,10-dimethyl-5-oxo-1,5-dihydro-2H-chromeno[3,4-c]pyridin-3(4H)-yl}carbonyl)-2-(trifluoromethoxy)phenyl]methanesulfonamide,
   N-[4-({8-[(3S)-3,4-dimethylpiperazin-1-yl]-7-methyl-5-oxo-1,5-dihydro-2H-chromeno[3,4-c]pyridin-3(4H)-yl}carbonyl)-2-(trifluoromethoxy)phenyl]ethanesulfonamide,
   N-[4-({8-[(3S)-3,4-dimethylpiperazin-1-yl]-'7,10-dimethyl-5-oxo-1,5-dihydro-2H-chromeno[3,4-c]pyridin-3(4H)-yl}carbonyl)-2-(trifluoromethoxy)phenyl]ethanesulfonamide,
   N-[4-({8-[(3S)-3-ethyl-4-methylpiperazin-1-yl]-7-methyl-5-oxo-1,5-dihydro-2H-chromeno[3,4-c]pyridin-3(4H)-yl}carbonyl)-2-(trifluoromethoxy)phenyl]methanesulfonamide, and
   N-[4-{[7-methyl-5-oxo-8-(3,3,4-trimethylpiperazin-1-yl)-1,5-dihydro-2H-chromeno[3,4-c]pyridin-3(4H)-yl]carbonyl}-2-(trifluoromethoxy)phenyl]methanesulfonamide.

3. A method for inhibiting MTHFD2 in a subject, comprising administering to a subject an effective amount of the compound or a salt thereof according to claim 1.

4. A method for treating breast cancer, comprising administering to a subject in need thereof a therapeutically effective amount of the compound or a salt thereof according to claim 1.

5. A pharmaceutical composition comprising the compound or a salt thereof according to claim 1 and a pharmaceutically acceptable carrier.

* * * * *

UNITED STATES PATENT AND TRADEMARK OFFICE
CERTIFICATE OF CORRECTION

PATENT NO. : 10,774,087 B2
APPLICATION NO. : 16/463792
DATED : September 15, 2020
INVENTOR(S) : M. Ota et al.

It is certified that error appears in the above-identified patent and that said Letters Patent is hereby corrected as shown below:

In the Claims

| Column | Line | |
|---|---|---|
| 46 | 25 | In Claim 1, change "-'7," to -- -7, -- |
| 46 | 33 | In Claim 1, change "-'7," to -- -7, -- |

Signed and Sealed this
Twenty-fourth Day of May, 2022

Katherine Kelly Vidal
*Director of the United States Patent and Trademark Office*